United States Patent [19]

Asberom et al.

[11] Patent Number: 5,362,728
[45] Date of Patent: Nov. 8, 1994

[54] 4,5-BRIDGED-2,3,4,5-TETRAHYDRO-1H-3-BENZAZEPINE-7-OLS AND DERIVATIVES AND COMPOSITIONS AND METHODS EMPLOYING SUCH COMPOUNDS

[75] Inventors: Theodros Asberom, Morris Plains; Edward O'Connor, Hoboken; Joel G. Berger, Cedar Grove; John W. Clader, Cranford, all of N.J.

[73] Assignee: Schering Corporation, Kenilworth, N.J.

[21] Appl. No.: 915,710

[22] PCT Filed: Jan. 31, 1991

[86] PCT No.: PCT/US91/00503
§ 371 Date: Jul. 29, 1992
§ 102(e) Date: Jul. 29, 1992

Related U.S. Application Data

[63] Continuation-in-part of Ser. No. 474,428, Feb. 2, 1990, abandoned.

[51] Int. Cl.$^5$ .................. A61K 31/55; C07D 223/18; C07D 223/32
[52] U.S. Cl. ...................... 514/217; 540/586
[58] Field of Search .................. 540/586; 514/217

[56] References Cited

U.S. PATENT DOCUMENTS

| | | | |
|---|---|---|---|
| 3,393,192 | 7/1968 | Walter | 540/595 |
| 3,609,138 | 9/1971 | Mull | 540/595 |
| 3,752,892 | 8/1973 | Hoegerle et al. | 514/213 |
| 4,011,319 | 3/1977 | Kaiser | 514/213 |
| 4,284,555 | 8/1981 | Gold | 540/595 |
| 4,477,378 | 10/1984 | Gold | 540/595 |
| 4,973,586 | 11/1990 | Berger et al. | 514/217 |

FOREIGN PATENT DOCUMENTS

| | | | |
|---|---|---|---|
| 1118688 | 2/1967 | United Kingdom. | |
| 1221324 | 2/1971 | United Kingdom. | |
| 87/04430 | 7/1987 | WIPO | C07D 223/14 |
| 89/00561 | 1/1989 | WIPO | C07D 223/32 |

*Primary Examiner*—Mukund J. Shah
*Assistant Examiner*—Philip I. Datlow
*Attorney, Agent, or Firm*—James R. Nelson; Edward H. Mazer; Anita W. Magatti

[57] ABSTRACT

Novel benzazepines of the formula I:

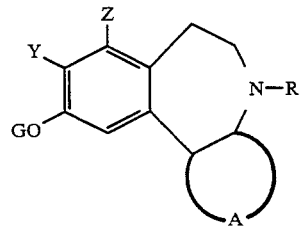

or a pharmaceutically acceptable salt thereof, wherein R represents H, alkyl, allyl or

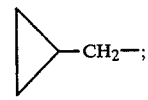

A represents —$[CR^1R^2]_n$—; n represents 3 or 4;
$R^1$ and $R^2$ may be the same or different and each independently represents H, OH, atkyl, alkoxy, phnenyl or substituted phenyl, with the proviso that $R^1$ and $R^2$ on the same carbon atom are not both OH, or $R^1$ and $R^2$ on the same carbon atom together represent=O;
G represents H, $R^3$(CO)— or ArNHCO—;
$R^3$ represents H, alkyl, alkoxy, phenyl or substituted phenyl;
Ar represents phenyl or substituted phenyl; and
Y and Z may be the same or different and each is independently selected from H, halo, alkyl, alkoxy or halpalkyl;
the pharmaceutically acceptable salts thereof, and pharmaceutical compositions thereof, useful in the treatment of psychoses, drug dependence, D1 dependent neurological disorder or pain are disclosed.

11 Claims, No Drawings

4,5-BRIDGED-2,3,4,5-TETRAHYDRO-1H-3-BENZAZEPINE-7-OLS AND DERIVATIVES AND COMPOSITIONS AND METHODS EMPLOYING SUCH COMPOUNDS

This application is a continuation-in-part of prior application Ser. No. 07/474,428 filed Feb. 2, 1990, now abandoned.

BACKGROUND OF THE INVENTION

This invention relates to 4,5-bridged-2,3,4,5-tetrahydro-1H-3-benzazepine-7-ols and derivatives and compositions and method employing such compounds.

Substituted 1-phenyl-2,3,4,5-tetrahydro-1H-3-benzazepines have been described in the art. For example, see U.S. Pat. Nos. 3,393,192, 3,609,138, 4,011,319, 4,284,555 and 4,477,378 well as British Patent 1,118,688. The activities discussed for the compounds disclosed in these patents include anti-bacterial effects, central nervous system effects and hypotensive effects.

British Patent Specification No. 1 221 324 discloses compounds of the formula:

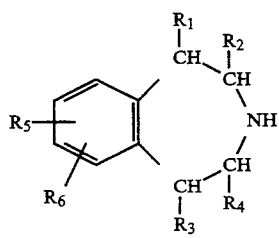

wherein $R_1$ and $R_2$, independently of each other, represent a hydrogen atom, an alkyl group containing maximally 6 carbon atoms, a cycloalkyl group having from 3 to 7 carbon atoms as ring members or a phenyl group optionally substituted by a chlorine, flourine or bromine atom and/or by an alkyl group containing maximally 6 carbon atoms, $R_3$ and $R_4$ have the meanings given above for $R_1$ and $R_2$ or together they represent a trimethylene or tetramethylene radical, $R_5$ represents a hydrogen or a halogen atom, and $R_6$ represents a hydrogen, chlorine, flourine or bromine atom, an alkyl group containing maximally 6 carbon atoms or a triflouro methyl group, provided that no more than two of the symbols $R_1$, $R_2$, $R_3$ and $R_4$ may simultaneously represent a cycloalkyl group or an optionally substituted phenyl group. These compounds are disclosed as intermediates for the production of N-guanidinoalkyl derivatives which have antihypertensive properties, and the unsubstituted 2,3,4,5-tetrahydro-1H-3-benzazepine compound is disclosed as being useful as an intermediate for the production of arylsulphonyl ureas having a hypoglycaemic action. In addition, 7-chloro-2,3,4,5-tetrahydro-1H-3-benzazepine and the salts thereof are said to have an anorexigenic action.

WO 87/04430 and WO 89/00561 disclose compounds of the formula:

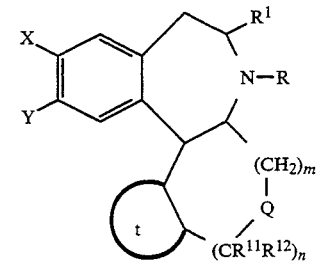

wherein R is hydrogen, alkyl, —CH₂CH=CH₂ or

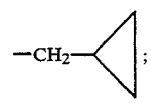

$R^1$, $R^{11}$ and $R^{12}$ may be the same or different and each is hydrogen or alkyl;

Q is methylene, —O— or —S—;

m and n are independently variable and each may have a value of 0, 1 or 2, with the provisos that the sum of m and n is not greater than 3, that m may not equal zero when Q is —O— or —S—;

X is hydrogen, halo, alkyl, alkylthio, alkylsulfinyi, alkylsulfonyl, hydroxy, alkoxy or triflouromethyl;

Y is hydrogen, hydroxy, alkoxy,

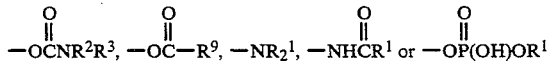

where $R^1$ is as defined above;

W is hydrogen, hydroxy or alkoxy;

ring t represents a fused thiophene or fused benzene ring, said fused benzene ring optionally being substituted with a substituent Z as defined below;

$R^2$ and $R^3$ are independently hydrogen (provided that both are not hydrogen), alkyl, aralkyl, cycloalkyl, aryl, hydroxyalkyl, or alkoxyalkyl;

in addition, when one of $R^2$ and $R^3$ is as defined above, the other may be —$R^4NR^5R^6$ {wherein $R^4$ is alkanediyl, $R^5$ is hydrogen or alkyl and $R^6$ is alkyl, or $R^5$ and $R^6$ together with the nitrogen atom form a 1-azetidinyl, 1-pyrrolidinyl. 1-piperidinyl, 1-(4-alkyl-piperazinyl), 4-morpholinyl or 1-(hexahydroazepinyl) group};

in further addition. $R^2$ and $R^3$ together with the nitrogen atom may form a 1-azetidinyl, 1-pyrrolidinyl, 1-piperidinyl, 4-morpholinyl, 1-(4-alkylpiperazinyl), 1-(4-alkoxyalkylpiperazinyl), 1-(4-hydroxyalkylpiperazinyl), 1-(3-hydroxyazetidinyl), 1-(3-alkoxyazetidinyl), 1-(3-hydroxypyrrolidinyl), 1-(3-alkoxypyrrolidinyl), 1-(3-or 4-hydroxypiperidinyl), 1-(3- or 4-alkoxypiperidinyl), 4-(4-oxopiperidinyl) or 1-(3-oxopyrrolidinyl) ring;

in still further addition, when $R^2$ is hydrogen, $R^3$ may be —$CHR^7CO_2R^8$, wherein $R^7$ and $R^8$ are independently hydrogen, alkyl or aralkyl;

$R^9$ is alkyl, aralkyl, aryl, alkoxyalkyl, aryloxyalkyl, aralkoxyalkyl, cycloalkylalkyl, alkoxycarbonylalkyl. cycloalkyl, 1-adamantyl, cycloalkoxyalkyl. alkoxy, aralkoxy, cycloalkoxy, aryloxy or '$CHR^7NHR^8$ {wherein $R^7$ and $R^8$ are defined above}; and Z is X as defined above, amino, alkylamino or

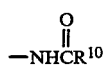

wherein R[10] is hydrogen, alkyl or aryl}. These compounds are disclosed as being useful in treating psychoses, depression, pain and hypertension.

SUMMARY Of THE INVENTION

It has now surprisingly been found that compounds of the formula I possess analgesic, antiaggressive and general tranquilizing properties:

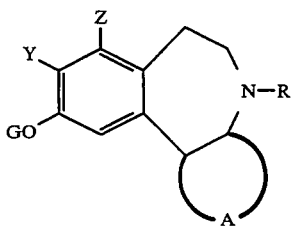

or a pharmaceutically acceptable salt thereof, wherein
R represents H, alkyl, allyl or

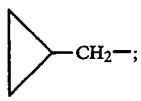

A represents —[$CR^1R^2$]$_n$—;
n represents 3 or 4;
$R^1$ and $R^2$ may be the same or different and each independently represents H, OH, alkyl, alkoxy, phenyl or substituted phenyl, with the proviso that $R^1$ and $R^2$ on the same carbon atom are not both OH, or $R^1$ and $R^2$ on the same carbon atom together represent=O;
G represents H, $R^3$(CO)— or ArNHCO—;
$R^3$ represents H, alkyl, alkoxy, phenyl or substituted phenyl;
Ar represents phenyl or substituted phenyl; and
Y and Z may be the same or different and each is independently selected from H, halo, alkyl, alkoxy or haloalkyl.

Ring A preferably represents

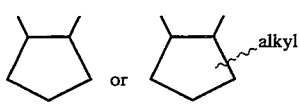

more preferably, ring A represents

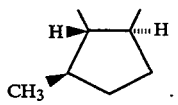

The Squiggly-line indicates that the group attached thereto may be in either of its relative configurations, i.e., R or S configuration, or may represent a mixture of such isomers. The squiggly line-drawn into the ring indicates that the group attached thereto may be in any of the available ring positions.

In another embodiment ring A preferably represents

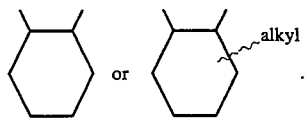

R is preferably methyl and Z is preferably H or chloro. Y is preferably chloro or methyl, and G preferably represents H or ArNHCO—.

A preferred subgenus of the compounds of the invention have the structural formula:

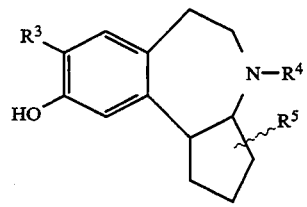

wherein $R^3$ is halo or alkyl; $R^4$ is H or methyl; and $R^5$ is H or alkyl; and pharmaceutically acceptable salts thereof.

Preferred compounds of the invention include:

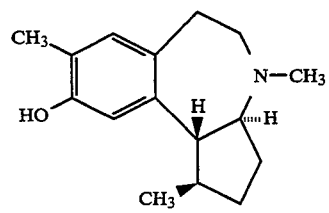

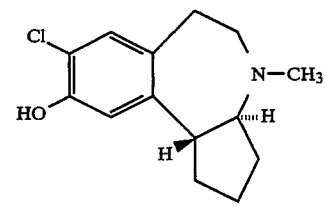

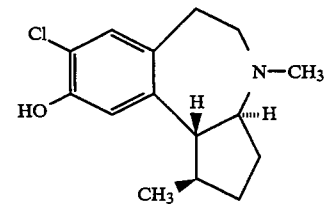

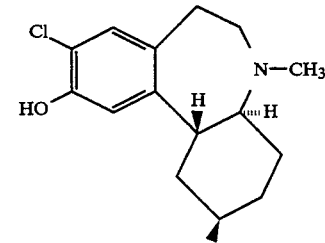

-continued

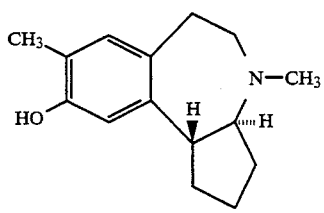

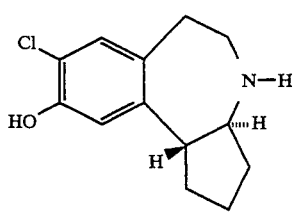

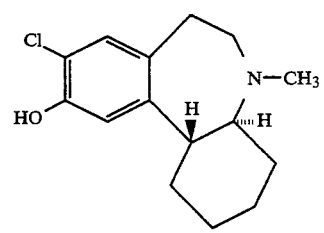

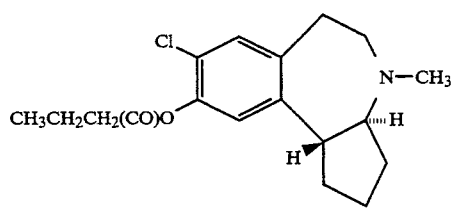

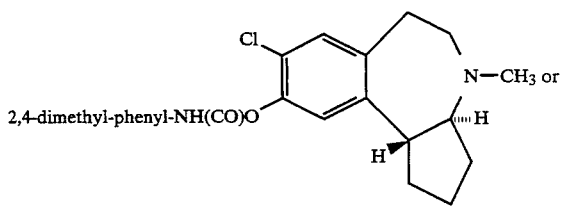

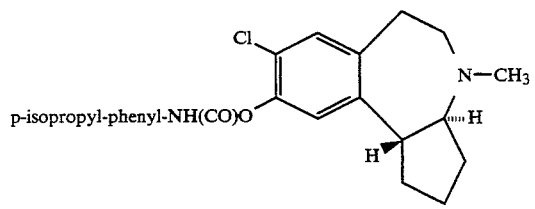

or a pharmaceutically acceptable salt of such compounds, e.g., a hydrochloride salt.

Particularly preferred compounds are of the structural formula

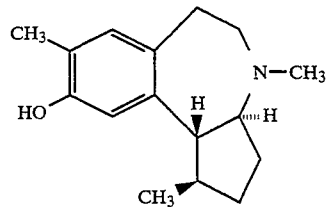

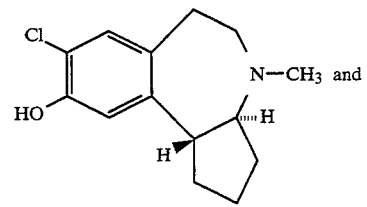

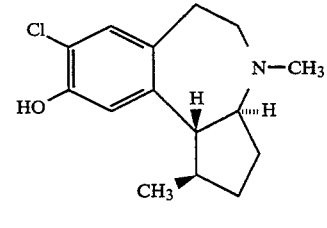

or a pharmaceutically acceptable salt of such compounds, e.g., a hydrochloride salt.

The invention also involves a pharmaceutical composition comprising a compound of formula I in combination with a pharmaceutically acceptable carrier and methods for treating psychoses, for treating drug dependence, for treating a mammal suffering from a D1 dependent neurological disorder, and for providing analgesia in a mammal, which comprises administering to the mammal an effective amount of a compound of formula I for such purpose.

DETAILED DESCRIPTION OF THE INVENTION

Compounds according to formula I may exist as diastereomers. Specifically, the fused ring system of formula I represented by ring A may be joined cis (formula II) or trans (formula III) and are, therefore, also diastereomers:

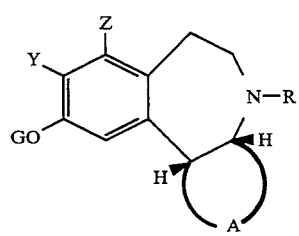

or

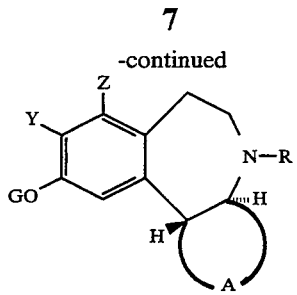

The trans form (formula III) of the compounds of formula I is a preferred embodiment. It is noted that, when $R^1$ and $R^2$ on the same carbon atom are different, e.g., H and $CH_3$, respectively, at least one other asymmetric center exists in the compounds of the invention. All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization or HPLC.

Compounds of formulas I can exist in unsolvated as well as solvated forms, including hydrated forms. In general, the solvated forms, with pharmaceutically acceptable solvents such as water, ethanol and the like are equivalent to the unsolvated forms for purposes of this invention.

The compounds of formulas I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide. potassium carbonate, ammonia and sodium bicarbonate. The free base forms differ from their respective salt forms somewhat in certain physical properties, such as solubility in polar solvents, but the salts are otherwise equivalent to their respective free base forms for purposes of the invention.

When utilized herein and in the appended claims, the following terms, unless otherwise specified, have the following meanings:

alkyl (including the alkyl portions of alkoxy and haloalkyl) represents a straight or branched, saturated hydrocarbon chain having from 1 to 8, preferably from 1 to 6, carbon atoms;

alkoxy - represents an alkyl group attached to a molecule through an oxygen atom (alkyl—O—);

cycloalkyl - represents a saturated carbocyclic ring having from 3 to 8, preferably from 3 to 6 carbon atoms;

halo - represents fluoro, chloro, bromo or iodo;

haloalkyl - represents an alkyl group as defined above wherein 1 to 3 hydrogens thereof have been replaced with a halo moiety, e.g., triflouromethyl, 2-chloroethyl, etc.; and substituted phenyl - represents a phenyl group in which 1 to 3 hydrogen atoms thereof are replaced by the same or different substituents independently chosen from hydroxy, alkyl, halo, nitro, alkoxy, haloalkyl including trifluoromethyl, cyano, cycloalkyl, SH, $S(O)_pR^a$ [wherein p is 0, 1 or 2 and $R^a$ is alkyl].

The compounds of formula I above may be prepared by the methods described below with reference to Schemes 1,2 and 3, wherein A, G, Y, Z and R are as defined above, unless otherwise indicated:

SCHEME 1

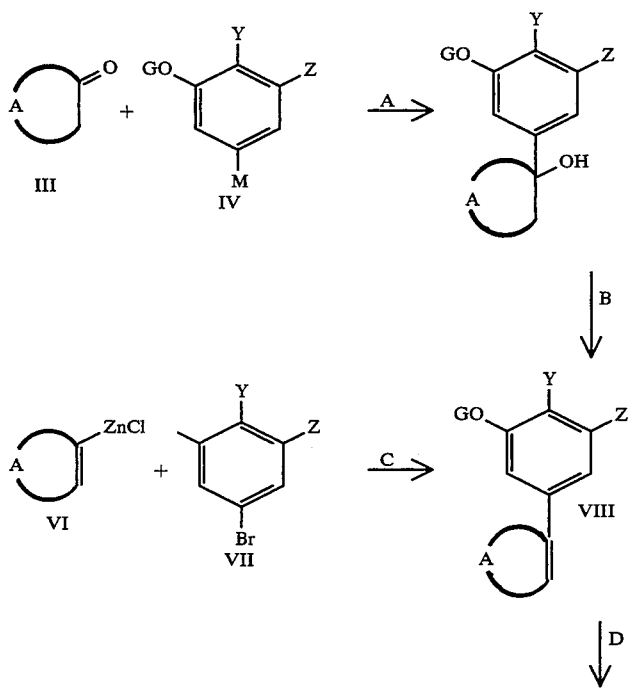

SCHEME 1 -continued

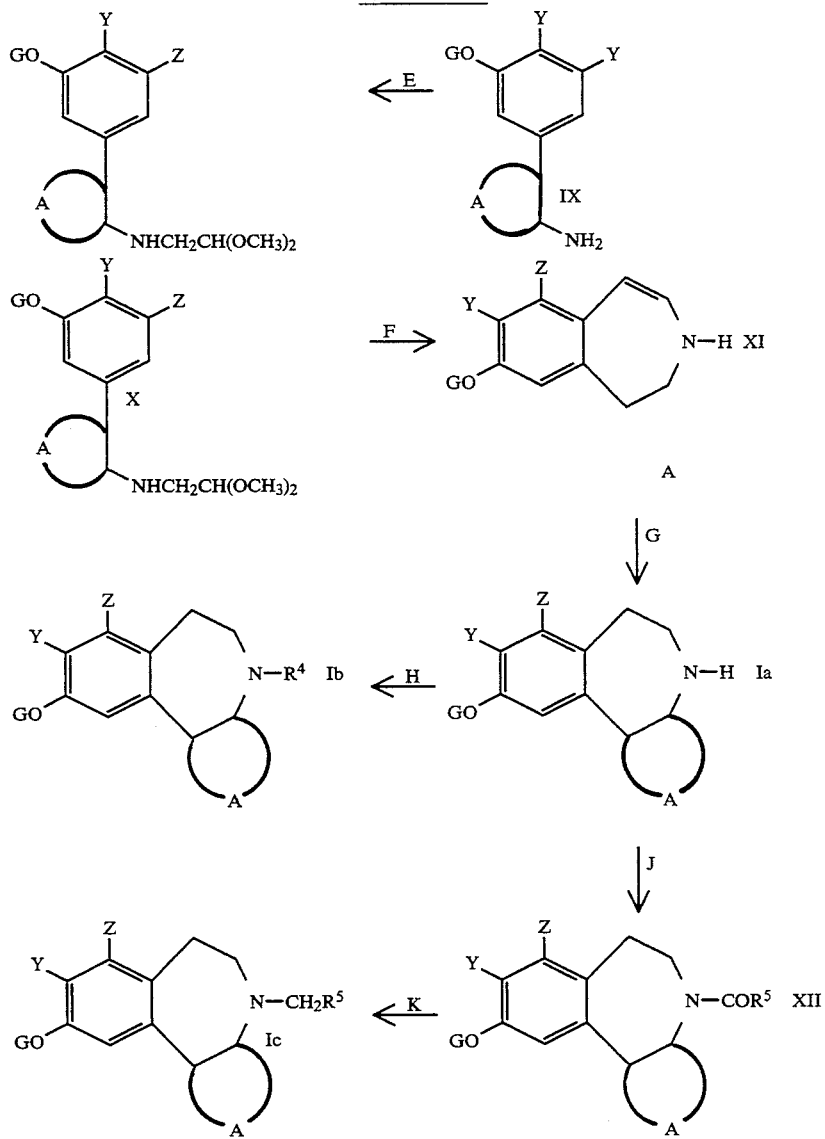

In step A of Scheme 1 above, the compounds of formulas III and IV are reacted neat or in a suitable solvent such as an ether solvent, e.g., tetrahydrofuran (THF) or diethyl ether, to form a compound of formula V. M represents a metallic group such as Li or MgX where X is halo. The temperature may range from about 20° to about 65° C.

In Step B, the compound of formula V is dehydrated to form a compound of formula VIII using an appropriate dehydrating agent such as an acid, e.g. para-toluenesulfonic acid, methanesulfonic acid, etc. The reaction may be run in a hydrocarbon solvent such as toluene, benzene, cyclohexane, etc. The reaction is preferably run at elevated temperatures such as from about 80° to about 130° C., with simultaneous removal of water.

The compound of formula VIII may alternatively be prepared by reacting compounds of formulas VI and VII: in step C of Scheme 1. The conditions for reaction step C are basically the same as those described above for step A.

The compound of formula VIII may then be reacted in step D with borane-methylsulfide complex $(BH_3 \cdot (CH_3)_2S)$. This reaction may be run in an ether solvent such as diglyme. The reaction is preferably performed at elevated temperatures of from about 50°-100° C. $H_2NOSO_3H$ is added to the reaction mixture as a solution in, preferably an ether solvent such as diglyme, and the mixture is heated at about 50°-100° C. for about 4 to 15 hours to form a IX.

The compound of formula IX is reacted in step E with a compound of the formula

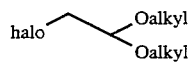

more preferably

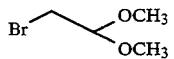

in the presence of an acid acceptor such as $K_2CO_3$ in a polar aprotic solvent, e.g., dimethylformamide at about 70°–100° C. for about 10–20 hours to form a compound of formula X.

The compound of formula X is reacted in step F with a strong acid such as methanesulfonic or trifluoroacetic acid in an appropriate hydrocarbon solvent or halocarbon solvent such as $CH_2Cl_2$ to form a compound of formula XI. The reaction is preferably run at low temperature, e.g. from about −25° C. to about +25° C.

The compound of formula XI is reacted in step G with an appropriate reducing agent such as lithium aluminum hydride, $NaCNBH_3$, etc. to form a compound of formula Ia. The reaction is preferably run in an alcohol solvent such as ethanol containing a small amount of acid to adjust pH to preferably 5–6. The acid is preferably a carboxylic acid such as acetic acid.

The compound of formula Ia, which is a compound of formula I of the invention wherein R is H, may be used to prepare other compounds of the invention. For example, the compound of formula may be reacted in step H with a compound of the formula $R^4X$ where $R^4$ is an alkyl group and X is a halo group to form a compound of formula Ib.

The compound of formula Ia may also be reacted in step J with a compound of the formula $R^5COX$, wherein $R^5$ represents an alkyl, alkoxy or cyclopropyl group and X is a halo group, in a solvent such as acetonitrile or chloroform at about 0°–25° C. to form a compound of formula XII. When $R^5$ is alkoxy, the product of the reduction is $R=CH_3$.

The compound of formula XII may then be reacted in step K with a carbonyl reducing agent such as lithium aluminum hydride or borane to form a compound of formula Ic. This may be done in an ether solvent such as diethyl ether or tetrahydrofuran at temperatures of from about 30° to about 65° C. for periods of from about 3–24 hours.

Scheme 2 below shows a series of reactions for preparing compounds of the invention having 6-membered fused rings, i.e., compound of formula I where n=4.

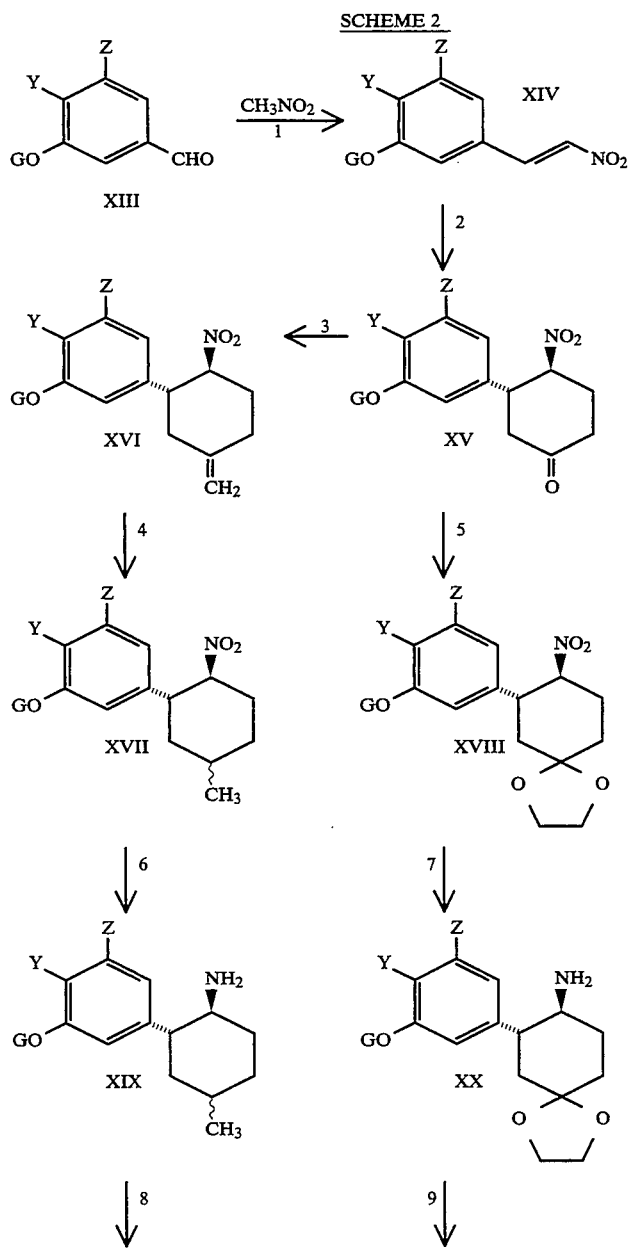

SCHEME 2

SCHEME 2

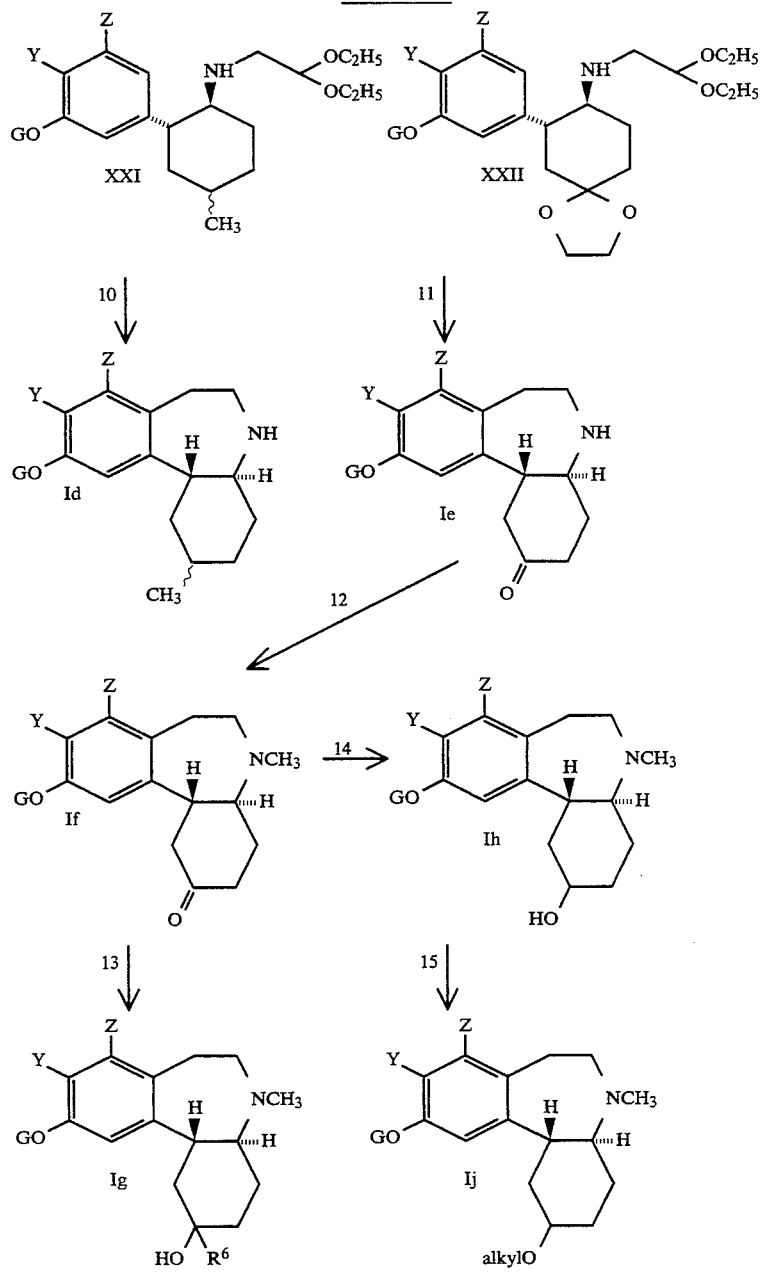

In step 1 of Scheme 2 a compound of formula XIII is reacted with $CH_3NO_2$ to form a compound of formula XIV. This reaction is preferably run in a carboxylic acid solvent such as acetic acid in the presence of a buffer such as ammonium acetate. The reaction is preferably run at a temperature of from about 25° C. to about 100° C.

The compound of formula XIV may then be reacted in step 2 with a compound of the formula

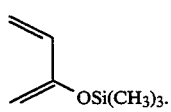

This reaction is preferably run at elevated temperatures of from about 100° C. to about 150° C. A base such as $K_2CO_3$ is then added to form a compound of formula XV.

The compound of formula XV may be reacted in step 3 with $(C_6H_5)_3P=CH_2$ at about −78° to about −20° C. to form a compound of formula XVI.

The compound of formula XV may also be reacted in step 5 of Scheme 2 with a ketalizing agent such as ethylene glycol in the presence of a catalytic amount of acid to form a compound of formula XVIII. Although the ketalizing agent ethylene glycol is shown is Scheme 2 others such as ethanol may be employed. Preferably, the reaction is run in a hydrocarbon solvent such as benzene or toluene at a temperature of from about 80° C. to about 130° C.

The compound of formula XVI may be reacted in step 4 of Scheme 2 with a reducing agent such as hydrogen in the presence of $Pt_2O$ at a pressure of from about 0 to about 40 psig in an appropriate alcohol solvent such as ethanol to form a compound of formula XVII.

The compounds of formulas XVII and XVIII may be reacted in steps 6 and 7 of Scheme 2, respectively, to form compounds of the formula XIX and XX, respectively. In both steps 6 and 7 an appropriate hydrogenating agent such as hydrogen or $NH_4+CO_2$— with palladium on carbon as a catalyst may be employed to form a compound of formula XIX or XX, respectively. This reaction is preferably run in an alcohol solvent such as ethanol.

The compounds of formula XIX and XX may be reacted in steps 8 and 9 to prepare compounds of formulas XXI and XXII, respectively. In both steps 8 and 9, the reactant employed is of the formula

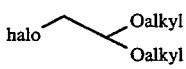

more preferably of the formula

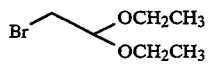

this reaction is preferably run in a solvent such as dimethylformamide at elevated temperatures of from about 80° C. to about 150° C. The latter formula is exemplified in Scheme 2 above but other compounds of the former formula may also be employed.

The compounds of formula XXI and XXII may be reacted in steps 10 and 11 of Scheme 2 to form the compounds of the formula Id and Ie, respectively. In steps 10 and 11 the compound of formula XXI or XXII is first reacted with a strong acid such as $CF_3CO_2H$, $H_2SO_4$, etc. The resulting product is then treated with an appropriate reducing agent such as $NaCNBH_3$, $NaBH_4$, etc., to form the compound of formula Id or Ie. The latter step is preferably performed in an alcoholic solvent, e.g., ethanol, at a pH of about 4–6.

The compounds of formula Id or Ie may be used as described in steps G, H, J and K of Scheme 1 above to prepare other compounds of the invention having R groups other than H.

The carbonyl group of the compound of formula Ie may also be employed to prepare other compounds of the invention as shown, for example, in steps 12, 13, 14 and 15 of Scheme 2. For example, in step 12, a compound of formula Ie is reacted with formaldehyde in formic acid as a solvent at elevated temperatures of from about 50° C. to about 125° C. to form a compound of formula If.

The compound of formula If may then be reacted in step 13 of Scheme 2 with a compound of the formula $R^6M$ wherein $R^6$ is alkyl, phenyl or substituted phenyl and M is a metal such as lithium or MgX where X represents halo to form a compound of formula Ig. This reaction may be run in an appropriate ether solvent such as THF or diethyl ether at a temperature of from about 0° C. to about 60° C.

The compound of formula If may also be reacted in step 14 with a reducing agent such as $NaBH_4$, $LiHlH_4$, etc., in an appropriate ether solvent such as THF at about 0° C. to about 60° C. to form a compound of formula Ih.

The compound of formula Ih may then be reacted in step 15 of Scheme 2 to form a compound of the formula Ij. In step 15, the compound of formula Ih is reacted with a compound of the formula alkylX, wherein X represents halo, in the presence of a base such as $K_2CO_3$. The reaction is preferably performed in an alcohol solvent such as ethanol at a temperature of from about 50° C. to about 100° C.

Scheme 3 below shows an alternative series of reactions for preparing a compound of formula IX. The compound of formula IX may then be employed as described in Scheme 1 above to prepare compounds of the invention.

SCHEME 3

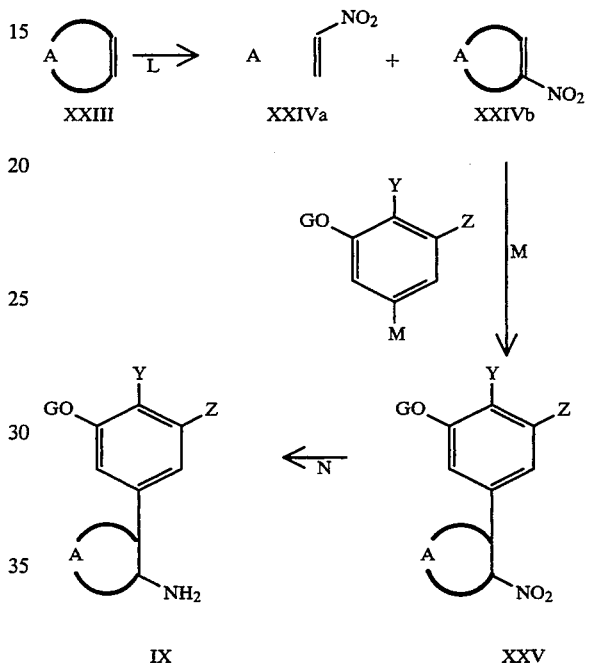

In step L of Scheme 3 above, a compound of the formula XXIII is reacted with $HgCl_2$ and $NaNO_2$ to form a compound of formula XXIVa and/or XXIVb. This reaction is preferably run in a carboxylic acid solvent such as acetic acid at a temperature of from about 30° C. to about 80° C.

In step M of Scheme 3 either of the compounds of formula XXIVa or XXIVb is employed depending upon what $(CR^1R^2)_n$ represents and the ultimate product desired to form a compound of formula XXV. The compound of XXIVa or XXIVb is reacted with the compound of formula IV wherein M represents a metal such as Li in the presence of an ether solvent such as tetrahydrofuran (THF) or diethyl ether. This reaction is preferably performed at a temperature of from about $-50°$ C. to about 50° C. more preferably from about $-10°$ C. to about 25° C.

The compound of formula XXV is then reacted in step N of Scheme 3 with an appropriate reducing agent such as lithium aluminum hydride or hydrogen in the presence of a platinum catalyst to prepare the compound of formula IX.

In the above processes, it is desirable and sometimes necessary to protect the groups in column 1 of Table 1 below. Conventional protecting groups are operable. Preferred protected groups appear in column 2 of Table 1.

TABLE 1

| 1. GROUP TO BE PROTECTED | 2. PROTECTED GROUP |
|---|---|
| \NH/ | \NCOalkyl/, \NCObenzyl/ |
| | \NCOphenyl/ |
| \CO/ | (cyclic acetal structures with O) |
| —OH | —O-(tetrahydropyranyl), —OCH$_2$phenyl, —OCH$_3$, OSi(CH$_3$)$_2$(t-Bu) |

Of course other protecting groups well known in the art may be used. After the reaction or reactions, the protecting groups may be removed by standard procedures well known in the art.

Also, R, R$^1$, R$^2$, Y, Z and GO groups in formula I may be varied by appropriate selection of starting materials from which the compounds are synthesized or by reacting a compound of formula I with a suitable reagent to effect the desired conversion of the substituent to another R. R$^1$, R$^2$, Y. Z or GO group. The latter procedure is particularly applicable for changing the substituents Y. For example, a halo substituent, e.g., a chloro group, may be added in place of hydrogen by reaction with a halogenating agent (e.g., achlodnating agent) such as sulfuryl chloride in a non-reactive solvent. A hydroxymethyl substituent in the Y position may be added in place of hydrogen by reaction with formaldehyde in a suitable solvent system, e.g., in a mixed solvent system consisting dimethoxyoxyethane and aqueous potassium hydroxide, preferably at an elevated temperature. Such a hydroxymethyl substituent may be reduced to an Y methyl group by reaction with a catalyst such-as palladium hydroxide in a hydrogen atmosphere under pressure. Compounds where Y and/or Z are alkyl can be prepared from corresponding compounds where Y and/or Z are bromo by reaction with an alkyl metallic compound, e.g., alkyl lithium. Other substitutions may be accomplished using standard techniques.

The antipsychotic activity of the compounds of the invention may be demonstrated in the following protocol.

CONDITIONED AVOIDANCE SUPPRESSION IN RATS

Clinically active antipsychotic drugs are known to depress discrete trial avoidance behavior at doses that do not retard escape response (Ann. N.Y. Acad. Sci. 66, 740 (1957)). A series of experiments was carded out to assess the ability of the compounds of this invention to suppress the conditioned avoidance response (CAR) in rats.

MATERIALS AND METHODS

Rats were required to jump onto a platform located 6.75 inches (17.15 cm) above the grid floor of an experimental chamber in response to a 5-second tone to avoid a 10-second foot shock (0.6 mA). Each experimental session consisted of 20 such trials presented at 30-second intervals. A correct CAR is scored whenever the rat jumps onto the platform during the tone (prior to foot shock). An escape response is scored when the rat jumps onto the platform during a shock. A response failure is defined as the lack of an escape response during the 10-second shock period.

Groups of 6–8 rats were trained in two consecutive days (total of 40 trials). Rats that reached criterion on day 2 (correct CARs on 16 or more of the 20 trials) were treated with either a test drug or vehicle on day 3. Suppression of CAR was analyzed statistically using the Student's t-test comparing the performances of drug-treated to vehicle-treated rats. The minimal effective dose (MED) for each drug is defined as the lowest dose tested that significantly ($P \leq 0.05$) reduced avoidance responding.

SQUIRREL MONKEY CONDITIONED AVOIDANCE RESPONSE (CAR) TEST

This test is designed to measure the potency of candidate compounds in a primate species.

Male or female squirrel monkeys weighing 800–1200 g housed one per cage are utilized. Initially each monkey is taught to terminate a 3 mA electric shock delivered through the grid floor of the test cage and an overlapping tone by depressing a lever in the cage. The monkeys do not proceed to the second phase of testing unless they depress the lever during the shock component of the trials at least 75% of the time during 60 daily trials on three consecutive days.

In the second phase of the testing, a ten second tone is turned on prior to the shock component. A lever press during the sounding of the tone terminates the tone and prevents the occurrence of the shock component and is denoted as an "avoidance". Compound testing does not begin until the monkey makes at least 85% correct avoidances for five consecutive days.

The compound testing is commenced after three consecutive days of re-testing. The monkey first is injected or orally dosed with the vehicle only and re-tested to show that the vehicle does not affect the response of the monkey. The monkey must achieve at least an 85% correct avoidance before drug testing commences. If this minimal avoidance level is achieved, the next day the monkey is orally dosed or injected with the subject compounds in the appropriate vehicle and the number of avoidances are recorded. An animal is defined as having been "affected" by any drug treatment if there is a 50% loss of avoidance behavior relative to the performance of the animal when only the vehicle is injected. The minimal effective dose (MED) is defined as that dose producing an effect in at least 50% of the animals.

A test may be conducted to determine the effective potency of a compound in accordance with the present invention by comparing a compound of the invention to a known compound, (R)-(+)-8-chloro-2,3,4,5-tetrahydro-3-methyl-5-phenyl-1H-3-benzazepin-7-ol hemimaleate, denoted as Compound B (Sch 23390). A compound of the invention administered 60 minutes prior to the test is compared to compound B administered 30 minutes prior to test. Results are shown in Column 9 of Table 1 below.

COMPETITIVE INHIBITION ASSAY

Many compounds capable of effecting reproducible physiological changes in neural tissues are believed to operate by binding at one or more receptor sites. Compounds which interact strongly with these receptor sites in in vitro tests, using homogenates of the target organ or structure, are expected to exhibit similar properties when administered in vivo and are, therefore, candidates for continued study as potential therapeutic and/or diagnostic agents.

Binding of a compound to a receptor site, in vitro, is demonstrated by the specificity of binding and the saturability of the available sites. A methodology for characterization of D-1 and D-2 receptor binding and an interpretation of the data are described by Billard et al., Life Sciences 35, 1885 (1984) in which the binding of the benzazepine (R)-(+)-8-chloro-2,3,4,5-tetrahydro-3-methyl-5-phenyl-1H-3-benzazepin-7-ol hemimaleate (SCH 23390) to the dopamine D-1 receptor is characterized. A selectivity for D-1 receptor binding as compared to D-2 receptor binding is believed to confer the therapeutic advantage of avoiding troublesome and potentially irreversible neurological side effects associated with D-2 receptor occupancy.

MATERIALS AND METHODS

Tritiated SCH 23390 and tritiated spiperone (a potent D-2 receptor ligand) are obtained as described in the Billard et al. reference supra and serially diluted in 0.05M Tris buffer, pH 7.4, as required. Compounds of this invention are synthesized as disclosed herein and diluted in 0.05M Tris buffer, pH 7.4, as required.

TISSUE PREPARATION

Male Sprague-Dawley rats (200 to 250 g) from Charles River Breeding Laboratories, Mass. are used to obtain brain tissue. The rats are humanely sacrificed and their brains removed and placed on ice. Striatal tissue is excised, pooled, and homogenized (Brinkman Polytron, 10 sec) in 100 volumes (w/v) of ice cold 50 mM Tds buffer, pH 7.4 (at 25° C.). The homogenate is centrifuged at 20,000 xg for 10 min. The resultant pellet is rehomogenized in Tris buffer and centrifuged again. The final pellet is resuspended in 50 mM Tris buffer pH 7.4 containing 120 mM NaCl, 5 mM KCl, 2 mM CaCl$_2$, and 1 mM MgCl$_2$.

ASSAY

Polypropylene incubation tubes receive 100 μl of the individual test compounds at various concentrations dissolved or suspended in 0.05M Tris, pH 7.4 containing 4 mg/ml methylcellulose, 100 μl of a solution of $^3$H-SCH 23390 in Tris buffer (final reaction mixture concentration=0.3 nM) or 100 μl of a solution of $^3$H-spiperone in Tris buffer (final concentration=0.2 nM) and 800 μl of tissue suspension (ca. 3 mg/assay). Tubes are incubated at 37° C. for 15 minutes and rapidly vacuum filtered through Whatman GF/B filters and rinsed 4 times with 4 ml of ice cold 50 mM Tds buffer, pH 7.4. The filters are transferred to scintillation vials, equilibated with 10 ml of scintillant (Scintosol, Isolab, Inc.) for 16 hours at 25° C. and the radioactivity determined in a liquid scintillation counter, K$_i$ values are determined as described by Billard et al. using the relationship K$_j$=IC$_{50}$/(1+([L]/K$_D$)) wherein IC$_{50}$=concentration of test drug necessary to displace 50% of specifically bound $^3$H-Sch 23390, [L]=concentration of radioligand used in the assay, and K$_D$=dissociation constant.

RESULTS

The inhibition constants (Ki) determined from the assays for a series of compounds of the invention are as shown in columns 7 and 8 of Table 1 below.

TABLE 1

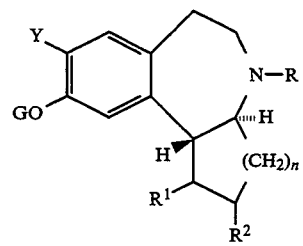

| | | | | | | Col. 7 | Col. 8 | Col. 9 |
| Col. 1 | Col. 2 | Col. 3 | Col. 4 | Col. 5 | Col. 6 | Ki (nM) | | CAR(MED) mpk p.o. |
| R | n | GO | R$^1$ | R$^2$ | Y | $^3$H-Sch23390 | $^3$H-Spip | Sq. Monkey @ 1 hr |
| H | 1 | HO | H | H | Cl | 96 | 1300 | |
| CH$_3$ | 1 | HO | H | H | Cl | 2.8 | 380 | >10 |
| CH$_3$ | 1 | 4-iPrC$_6$H$_4$NHCO$_2$ | H | H | Cl | 5.4 | 430 | |
| CH$_3$ | 1 | n-C$_4$H$_9$CO$_2$ | H | H | Cl | 24 | 177 | |
| CH$_3$ | 1 | 2,4(Me)$_2$C$_6$H$_3$NHCO$_2$ | H | H | Cl | 7.7 | 428 | >3 |
| CH$_3$ | 1 | HO | H | H | H | 335 | 2320 | |
| CH$_3$ | 2 | HO | H | H | CH$_3$ | 70 | 71000 | >10 |
| CH$_3$ | 1 | HO | CH$_3$ | H | Cl | 3 | 350 | >10 |
| CH$_3$ | 1 | HO | CH$_3$ | H | CH$_3$ | 14 | 840 | 3 |
| CH$_3$ | 2 | HO | H | CH$_3$ | Cl | 70 | >10,000 | >10 |

The comparatively small K$_i$ values of the compounds of the invention in the competitive binding assay with SCH 23390 indicate that the compounds of formula I bind strongly to the D-1 receptor site. The relatively high K$_i$ values for the D-2 site, for which spiperone is highly selective, indicate that the compounds are not specifically bound to that receptor site.

Selective activity for D1 receptors is indicative of these compounds potential use as D1 antagonists in treating disorders that may be lessened by D1 antagonists as discussed in Beaulieu, Canadian J. Neur. Sci. 1–4(3):402 (1987) and Waddington, Gen. Pharmac. 19(1):55 (1988). These disorders include disorders associated with stereotypic behaviors and drug dependence. D1 antagonists have been shown to block cocaine- and morphine-dependent pleasure sensations making the compounds of the present invention useful in treating drug dependence. Furthermore, although the precise mechanisms involved in a variety of movement disorders are unknown, it is generally accepted that they all use the striatum as a final common pathway. The striatum contains the highest density of D1 receptors suggesting that movement disorders may be treated using D 1 antagonists. Consequently, the compounds of the present invention have potential utility in treating movement disorders such as Parkinson's disease, Huntington's chorea and tardive dyskinesias. Additionally, D1 antagonists have potential utility as inhibitors of disorders associated with repetitive, stereotypic behavior such as Lesch-Nyhan disease.

The antidepressive method of the invention is demonstrated, for example, by test procedures which measure a compound's effect on tetrabenazine (TBZ)-induced ptosis in mice or which measure a compound's effect on mudcide activity in rats as discussed below.

ANTIDEPRESSANT POTENTIAL

EFFECTS ON TETRABENAZINE (TBZ)-INDUCED PTOSIS IN MICE

Clinically active antidepressant drugs are known to block TBZ-induced ptosis in mice (Psychosomatic Medicine, Nodine and Moyer, Eds., Lea and Febiger, Philadelphia, 1962, pp 683–90). Activity in this test is used to predict anti-depressant activity in man.

METHODS AND MATERIALS

Groups of 5 mice are administered test drugs followed 30 minutes later by ip injection of tetra-benazine, 30 mg/kg. Thirty minutes later, the degree of ptosis is evaluated. Percent blockade of each treated group is used to determine $ED_{50}$'s defined as that dose which prevents ptosis in 50% of mice. $ED_{50}$'s and 95% confidence limits are calculated by probit analysis.

EFFECTS ON MURICIDAL BEHAVIOR IN RATS

Blockade of mudcidal (mouse-killing) behavior in rats is used as a measure of evaluating the anti-depressant activity of drugs (Int. J. Neuro-pharmacol., 5, 405–11 (1966)).

METHODS AND MATERIALS

Groups of 5 rats are administered test drug intraperitonially and are tested 30 and 60 minutes later for presence of muricidal behavior. Percent blockade of each treated group using data obtained at both these time points is calculated and dose-response data are used to determine each $ED_{50}$. $ED_{50}$ is defined as that dose which blocks muricide behavior in 50% of treated rats and is calculated using probit analysis.

The analgesic effect of the compounds of formula I and the method for providing analgesia may be exemplified by the Acetic Acid Writhing Test in mice described below.

ACETIC ACID WRITHING TEST IN MICE

The blockade of writhing induced by the intraperitoneal injection of acetic acid is an established experimental animal model for the screening of antinociceptive drugs (drugs which prevent the appreciation or transmission of pain sensations). See Hendershot et al., *J. Pharmacol. Exp. Therap.* 125:237, (1959) and Koster et al., *Fed. Proc.* 18:412, (1959).

METHODS AND MATERIALS

Compounds to be tested are dissolved or suspended in aqueous 0.4% methylcellulose vehicle. For oral administration, dosages are prepared for delivery of the selected weight of compound in a total volume of 20 mg/kg of body weight. For subcutaneous or intraperitoneal administration, dosages are prepared for delivery of the selected weight of compound in a volume of 10 ml/kg of body weight.

The test procedure is that described by Hendershot et al., supra, except that acetic acid is substituted for phenylquinone. Groups of five male CF1 mice (20–26 g.) are dosed orally with test drug and injected 15 minutes later with 0.6 ml aqueous aqueous acetic acid (10 mg/kg). The mice are placed in a large observation beaker and the number of widthes for each animal is counted during a 10 minute interval starting 3 minutes after injection of acetic acid. A writhe is defined as a sequence of arching of the back, pelvic rotation and hindlimb extension. Initial screening is performed using a dosage of 30 mg/kg. If this dose affords 50% or greater reduction in the number of writhes compared to the control, the animal is considered to be protected, a dose response curve is developed using a logarithmic sequence of lower doses and an $ED_{50}$ is determined by interpolation.

The compounds of the invention are selective D1 receptor antagonists. D1 antagonists have been shown to block cocaine- and morphine-dependent pleasure sensations making the compounds of the present invention useful in treating drug dependence. The activity of the compounds of the invention in treating drug dependence may be demonstrated by the protocol described in Kleven, et al., *Psychopharmacology* (1988) 95: pp. 427–429 or by the procedure describe in Koob, et al., *Neuroscience Letters,* 79 (1987) pp. 315–320.

The active compounds can be administered orally, topically, parenterally, or by oral or intranasal inhalation. The preferred mode of administration is orally or intravenously.

The compounds can be administered in conventional oral dosage forms such as capsules, tablets, pills, powders, suspensions or solutions prepared with conventional pharmaceutically acceptable excipients and additives, using conventional techniques. Parenteral preparations, i.e., sterile solutions or suspensions are also made by conventional means. Inhalation administration can be in the form of a nasal or oral spray. Insufflation is also contemplated.

For preparing pharmaceutical compositions from the compounds described by this invention, inert, pharmaceutically acceptable carders can be either solid or liquid. Solid form preparations include powders, tablets, dispersible granules, capsules, cachets and suppositories. The powders and tablets may comprise from about 5 to about 70 percent active ingredient. Suitable solid carriers are known in the art, e.g., magnesium carbonate, magnesium stearate, talc, sugar, lactose. Tablets, powders, cachets and capsules can be used as solid dosage forms suitable for oral administration.

Liquid form preparations include solutions, suspensions and emulsions. As an example may be mentioned water or water-propylene glycol solutions for parenteral injection.

Liquid form preparation may also include solutions for intranasal administration.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration)in order to retard possible decomposition. The solid form preparations intended to be converted to liquid form may contain in addition to the active material, flavorants, colorants, stabilizers, buffers, artificial and natural sweeteners, dispersants thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

For preparing suppositories, a low melting wax such as mixture of fatty acid glycerides or cocoa butter is first melted, and the active ingredient is dispersed homogeneously therein as by stirring. The molten homogeneous mixture is then poured into convenient size molds, allowed to cool and thereby solidify.

Preferably, the pharmaceutical preparation is in unit dosage form. In such form, the preparation is subdivided into unit doses containing appropriate quantities of the active component, e.g., an effective amount to achieve the desired purpose.

When used orally or parenterally, the compounds of the invention can be administered in an amount ranging from about 0.02 mg/kg body weight to about 4.0 mg/kg body weight, preferably from about 0.1 mg/kg body weight to about 2.0 mg/kg body weight per day.

Determination of the proper dosage of a compound of the invention for a particular situation is within the skill of the art. Generally, treatment is initiated with smaller dosages that are less than the optimum dose of the compound, Thereafter, the dosage is increased by small increments until the optimum effect under the circumstances is reached. For convenience, the total daily dosage may be divided and administered in portions during the day if desired.

The amount and frequency of administration of the compounds of formula I and the pharmaceutically acceptable salts thereof will be regulated according to the judgment of the attending clinician considering such factors as age, condition and size of the patient as well as severity of the symptom being treated.

The invention disclosed herein is exemplified by the following preparative examples, which should not be construed to limit the scope of the disclosure. Alternative mechanistic pathways and analogous structures within the scope of the invention may be apparent to those skilled in the art.

Preparative Example 1

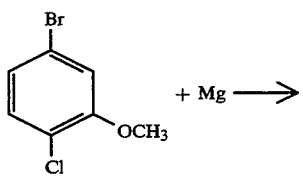

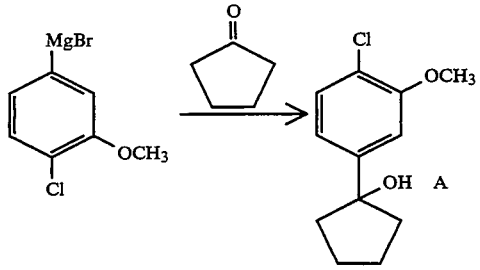

A 2l flask equipped with a 250 ml dropping funnel, stirrer, condenser, and thermometer was flame-dried, charged with magnesium turnings (35.2 g), and blanketed with argon. The dropping funnel was charged with a solution of 5-bromo-2-chloroanisole (250 ml, 270 g) in 600 ml of tetrahydrofuran, which was then added slowly to the magnesium turnings. Initiation of their reaction was rapid as evidenced by refluxing of the solvent. Addition was continued slowly, and the temperature of the reaction mixture was maintained at about 25° C. by use of an ice-water bath. Upon completion of the addition, the mixture was allowed to stir at room temperature for 1 hr, then a solution of cyclopentanone (100 g) in 100 ml of tetrahydrofuran (THF) was added with stirring at such a rate that the temperature remained at about 25° C. Upon completion of the addition, the mixture was allowed to stir overnight. 300 ml of a 20% aqueous solution of NH$_4$Cl was then added to the reaction mixture, which was then allowed to stir for 10 min. The organic layer was then separated, and solvent removed in vacuum to give the crude product as an amber oil. This product was purified by flash chromatography over 2 kg of silica gel eluting with hexane-ethyl acetate (95:5) to give 170 g of product of formula A above which was suitable for use in the next step.

Preparative Example 2

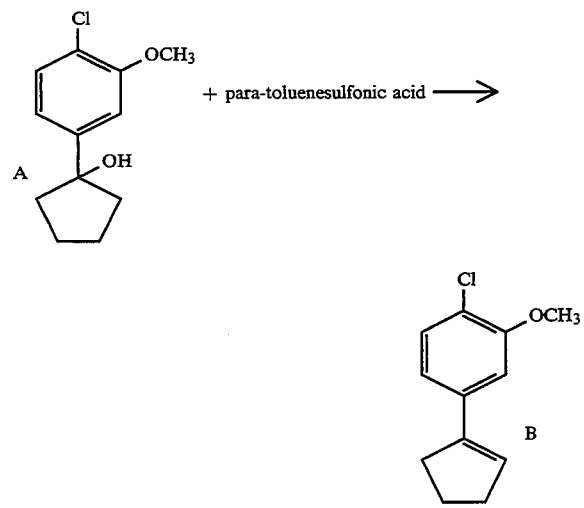

The product A of the Preparative Example 1 above was charged into a 500 ml round bottomed flask equipped with a magnetic stirrer bar and a Dean-Stark trap. Benzene (250 ml) and a few crystals of p-toluenesulfonic acid were added to the flask, which was then heated at reflux for 3 hrs, during which 14.5 ml of water had collected in the trap. The reaction mixture was allowed to cool to room temperature, and solvent removed under reduced pressure leaving a dark brown oil which was purified by chromatogrpahy over 2.5 kg of flash grade silica gel eluting with hexane initially followed by 95:5 hexane-ethyl acetate. Thusly, 112 g of product of formula B above was obtained. Mass spectrum M+/e=173.

Preparative Example 3

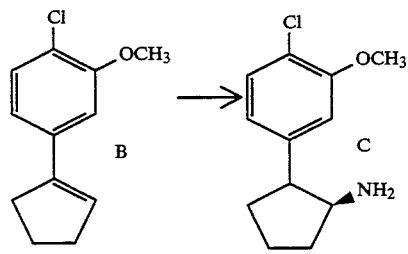

A 50 ml Schenk flask equipped with a stir bar, condenser, and 3 way-stopcock (all flame dried under vacuum) was charged with a 15 ml of diglyme and the product B of Preparative Example 2 above (3 g). The solution was freeze-thaw alegassed three times. $BH_3.SMe_2$ (2.4 ml of 2M solution in ethyl ether) was added with a syringe and the homogeneous reaction mixture heated to 65° C. As the temperature was increased the reaction mixture became cloudy and at 60° C. there was a substantial amount of white solid present.

The mixture was left stirring under argon overnight at 65° C. The reaction mixture now had become homogeneous and colorless.

Thin layer chromatography (TLC) analysis of the reaction mixture showed virtually complete consumption of starting material. $NH_2OSO_3H$ (1.68 g) was weighed out on a glove bag and diglyme (15 ml) added. The clear colorless solution was then added to the reaction mixture with a syringe and the oil bath temperature was raised to 100° C. At 100° C. the solution became yellow but was homogeneous; within 5 minutes, however, the solution turned an amber color as a white precipitate formed. The reaction mixture was allowed to stir at this temperature for about 3 hours.

The dark brown solution was allowed to cool to room temperature. 3N HCl (4 ml, pH∼1) was added and reaction mixture allowed to stir for 2 h after which it was diluted with 50 ml of $H_2O$ and extracted with diethyl ether ($Et_2O$) (3×50 mL). The aqueous layer was brought to pH 9 with solid KOH and then extracted with ethyl acetate (3×50 ml). The organic layer was added over $MgSO_4$, filtered, and the solvent removed under reduced pressure. TLC analysis of the crude reaction mixture showed one major spot purifications by column chromatography using 9:1 $CH_2Cl_2$—$CH_3OH$. Yielded 825 mg (26%) of pure amine of formula C above. Electron impact mass spectrum showed M+=225 and M+—$NH_3$ at 208.

Preparative Example 4

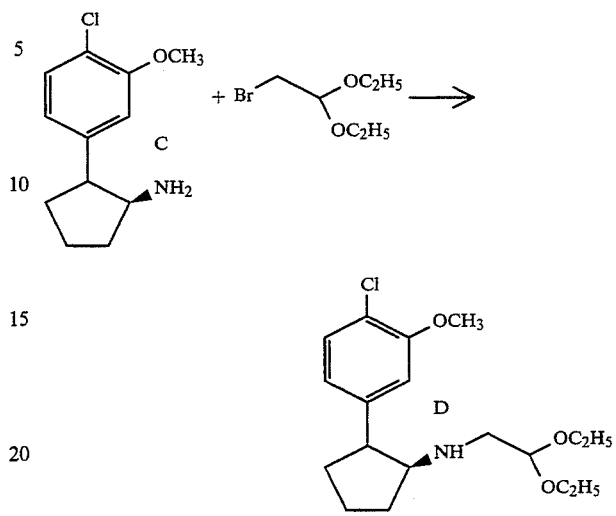

A 100 ml Round bottom flask equipped with a stir bar, reflux condenser, and three way stopcock was charged with the product C of Preparative example 3 above (3.06 g), bromoacetaldehyde diethylacetai (2.25 ml) anhydrous $K_2CO_3$ (9.4 g), and dimethyl formamide (50 ml). The mixture was heated at 80° C. for 20 h, and allowed to cool to room temperature. TLC analysis confirmed complete consumption of starting material.

The crude reaction mixture was added to 500 ml $Et_2O$, and the ether layer extracted with $H_2O$ (4×100 ml). The ether layer was dried over $MgSO_4$, filtered, and the solvent removed in vacuo. The remaining clear brown oil was loaded onto silica gel 60 in a scintered glass funnel and eluted with 100 ml $CH_2Cl_2$:$CH_3OH$ (95:5). The solvent was removed under reduced pressure leaving a brown oil. $^1H$ NMR showed mostly the desired alkylated amine of formula D above. This material (3.6 g) was utilized without further purification.

Example 1

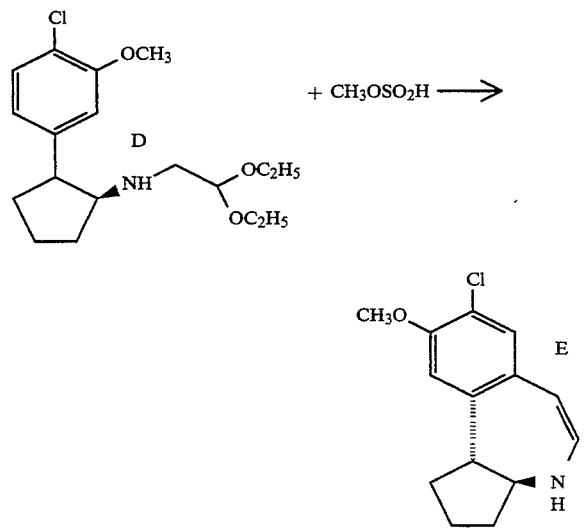

A 500 ml round bottom flask equipped with a stir bar was charged with 3.6 g of the product D of Preparative Example 4 and 300 ml of $CH_2Cl_2$. The solution was cooled to 0° C. and 44 ml of methanesulfonic acid added via syringe. The homogeneous reaction mixture was allowed to stir overnight while gradually warming to room temperature. The mixture was poured into 400 ml of water, and solid NaHCO3 added until bubbling had ceased. The layers were separated and, the aqueous layer extracted with CH2Cl2 (2-100 ml). The combined organic phase was dried over MgSO4, filtered and solvent removed under reduced pressure to give an orange-brown solid (2.5 g) of formula E above which was used in Example 2 below.

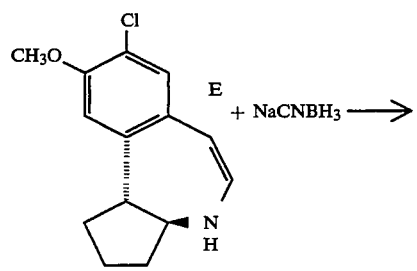

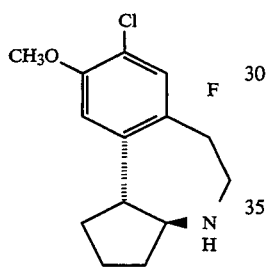

The product E of Example 1 (2.5 g), ethanol (25 ml) and NaCNBH3 (622 mg) was treated with glacial acetic acid (626 μl). The resulting mixture was allowed to stir at room temperature for 3 h, after which the solution was brought to pH 2 with 1M HCl, stirred for 1 h, and then brought to pH 8 with 3M NaOH. Solvent was removed under reduced pressure, and the resulting yellow oil taken up in CH2Cl2 (25 ml) and extracted with H2O. The organic layer was added over MgSO4, filtered, and solvent removed in vacuo to give an orange solid (2.2 g) of formula F above. Mass spectrum (chemical ionization M/e+ =252.

Example 3

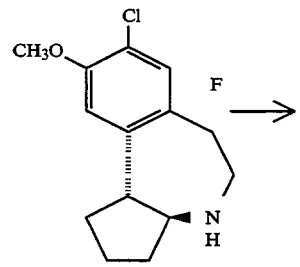

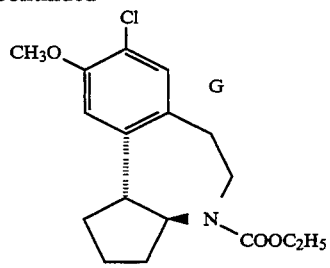

The product F of Example 2 above (125 mg), NaHCO3, and acetonoitrile (10 ml) was charged into a 100 ml flask equipped with a stirrer bar and septurn, and blanketed under argon stirrer bar and septum, and blanketed under argon. The stirred mixture was cooled in an ice-water bath, and ethyl chloroformate (53μl) was added dropwise via a 50 μl syringe. Upon completion of the addition, the mixture was allowed to warm to room temperature and stand for 2 hr. Solvent was removed under reduced pressure, and the residue partitioned between diethyl ether (50 ml) and water (15 ml). The ether layer was separated and added over K2CO3. Filtration and evaporation of solvent in vacuo gave a foamy off-white solid (160 mg) of formula G above.

Example 4

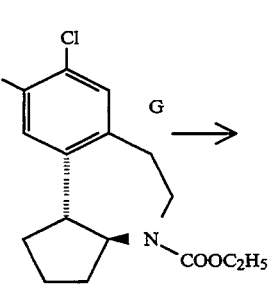

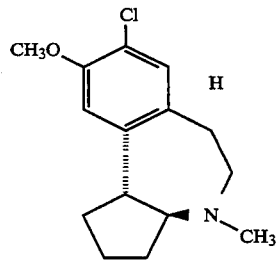

The product G of Example 3 above (160 mg), lithium aluminum hydride (38 mg) and anhydrous ether (15 ml) were combined in a 25 ml round bottom flask and heated at reflux for 16 hr. The cooled reaction mixture was then treated with water (38 μl), followed by 15% NaOH (38 μl ), then water (114 μl). The heterogeneous mixture was allowed to stir for 2 hr., then filtered through a pad of Celite. The pad was washed with 5 ml of THF, and the combined flitrates evaporated to give a pale yellow oil which was taken up in CH2Cl2, dried over Na2SO4 and filtered. Removal of solvent gave a light yellow oil which was chromatographed over a 20 mm X6 in. column of flash silica gel eluting with CHCl3—CH3OH (96:4) to give the product of formula H as a clear oil (93 mg).

Example 5

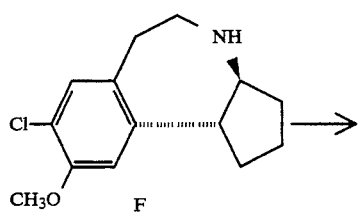

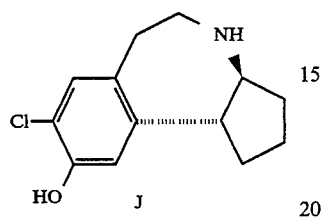

A 10 ml round-bottom flask was charged with the product F of Example 2 above (25 mg), $CH_2Cl_2$ (3 ml), and blanketed under argon. The solution was cooled to $-78°$ C. and $BBr_3$ (0.21 ml of 1M solution in $CH_2Cl_2$) added dropwise via syringe. The reaction mixture was allowed to stir at $-78°$ C. for 1 hr, then at room temperature for 2 hr. The mixture was then treated with 10 ml of methanol and allowed to stir for 30 minutes. Removal of solvent gave a yellow solid which was treated with 10% $Na_2CO_3$ followed by extraction into ethyl acetate. This solution was dried over $MgSO_4$, filtered, and solvent removed in vacuo to give the product of formula J as a brown solid. Mass spectrum $M/e+ = 237$.

Example 6

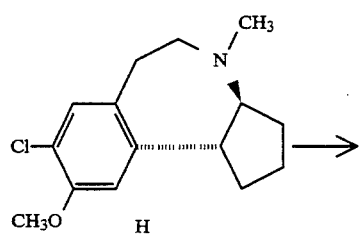

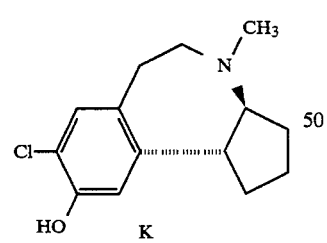

A solution of the product H of Example 4 above (3.37 g) in 150 ml of $CH_2Cl_2$ was cooled to 0° C., and blanketed under nitrogen. A 1 M solution of $BBr_3$ in $CH_2Cl_2$ (31.8 ml) was added dropwise via syringe. The solution was then allowed to stir for 5 h while warming to room temperature. Removal of solvent gave a foamy solid which was treated with 10% $NaHCO_3$ solution and extracted with chloroform. The aqueous layer was separated, extracted once with chloroform, and the combined chloroform extracts added over $Na_2SO_4$, filtered, and evaporated to give 2 g of product. 1 g of this material was dissolved in ethanol, and 7 ml of 1M HCl solution added. Removal of solvent gave a yellow-white solid which was triturated with cold ethanol to give a white product (700 mg) of formula K which was added in vacuo. M.p. >230°. Mass spectrum (electron impact) $M+/e=251$ (base).

Preparative Example 5

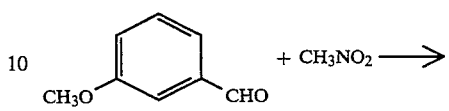

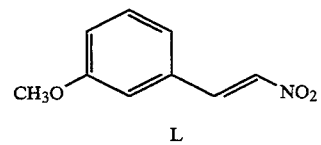

A solution containing 35.4 g (0.26 mol) of m-methoxybenzaldehyde, 17.7 g (0.29 mol) of nitromethane, 12.5 g (0.16 mol) of ammonium acetate, and 125 ml of glacial acetic acid was refluxed gently for 2 hr. The solution was cooled and poured into 800 ml of iced water. The precipitate was filtered and taken up in 500 ml of methylene chloride. The solution was dried over anhydrous magnesium sulfate and evaporated to yield a residue which was recrystallized from benzene, giving 8.1 g of yellow plates, m.p. 91°–92° C. (lit. 91°–92°). The mother liquor was evaporated and the remaining solid was washed with cold ether to give an impure yellow solid which was recrystallized from benzene to give 10.7 g of yellow plates of formula L above, m.p. 91°–92° C. The n.m.r. spectrum ($CDCl_3$) confirmed the structure of formula L. Total yield (8.1 g + 10.7 g) was 18.8 g (40%).

Preparative Example 6

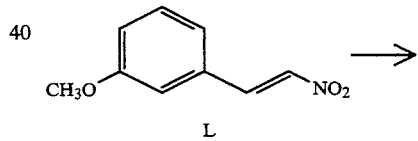

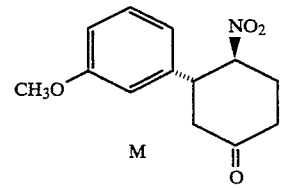

A neat mixture-containing 4.01 g (22.4 mmol) of m-methoxy-1-nitrostyrene (Osborn et al.; *J. Chem. Soc.* 4191–4203 (1956)) and 6.33 g (44.5 mmol) of 2-(trimethylsilyloxy)-1,3-butadiene was heated at 145° C. for 17 hr. Excess diene was removed in vacuo. The resulting dark, viscous oil was dissolved in 40 ml of methanol containing 80 mg of potassium carbonate and stirred overnight at room temperature. Removal of the solvent gave a dark solid which was chromatographed on a silica gel column using hexane - ethyl acetate - methylene chloride (45:25:30 v/v). The fractions containing the major product were combined and concentrated to 25 ml. This solution was heated to near boiling and 90 ml of hot hexane was added. The crystals which separated upon cooling were filtered and dried in vacuo to yield white needles (3.81 g, 68%), m.p. 112.5°–114° C. The n.m.r. spectrum (CDCl₃) confirmed the structure of formula M.

Preparative Example 7

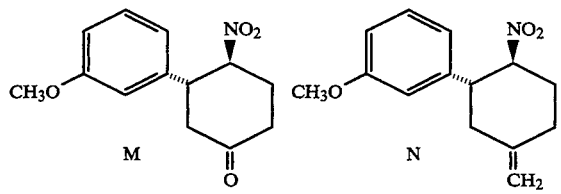

To a stirred suspension of 1.072 g (3.00 mmol) of methyltriphenylphosphonium bromide in 30 ml of tetrahydrofuran in a dry ice/acetone bath was added butyllithium (3.00 mmol) dropwise via syringe. The resulting yellow mixture was stirred at −20° C. for 1 hr. After cooling to −78°, a solution of 696 mg (2.79 mmol) of the compound of formula M in tetrahydrofuran (15 ml) was added over 8 minutes. The reaction mixture was allowed to warm to room temperature over 4 hr. and was then poured into 300 ml of 0.5M hydrochloric acid. The mixture was extracted with methylene chloride, washed with brine, dried (MgSO₄), and evaporated to give a yellow oil. Chromatography through a silica gel column using hexane - ethyl acetate - methylene chloride (72:18:10 v/v) yielded 499 mg (72%) of the compound of formula N as a light yellow oil. The n.m.r. spectrum (CDCl₃) confirmed the structure.

Preparative Example 8

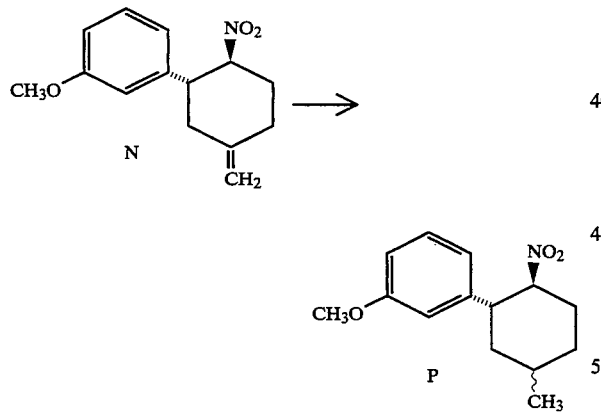

A solution of 2.904 g (11.74 mmol) of the compound of formula N in 225 ml of absolute ethanol containing 290 mg of platinum oxide was hydrogenated (40 psi) at room temperature for 6 hr. The catalyst was filtered off (celite) and the ethanol was evaporated to give 2.813 g (96.1%) of a yellow oil which was shown by TLC on silica gel using hexane - ethyl acetate (85:15 v/v) to be two products. A sample of the oil was chromatographed by preparative TLC on silica gel using hexane - ethyl acetate (92:8 v/v; 2 elutions). The enriched samples of each product thus attained were shown by 2-dimensional n.m.r. to be the axial-methyl and equatorial-methyl isomers of the compound of formula P, in a ratio of approximately 2 to 1, respectively, before chromatography.

Preparative Example 9

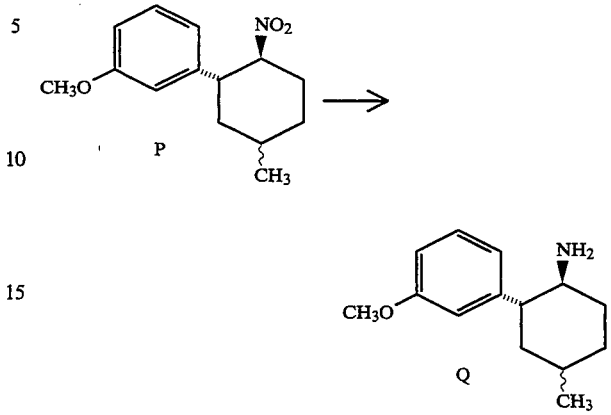

A solution of 2.810 g (11.3 mmol) of the compound of formula P, 8.64 g of ammonium formate, 280 mg of 10% palladium on carbon, and 150 ml of absolute ethanol was stirred at 70° C. overnight. The catalyst was filtered off (celite) and the ethanol was evaporated. To the residue was added water and sodium bicarbonate. The mixture was extracted with methylene chloride, dried (MgSO₄), and concentrated to give 2.404 g (97%) of the compound of formula Q as a yellow oil. The n.m.r. spectrum (CDCl₃) confirmed the structure.

Preparative Example 10

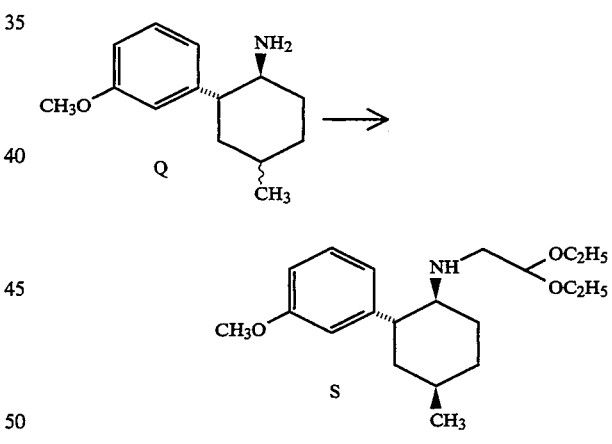

To a mixture of 2.404 g (10.96 mmol) of the compound of formula Q, 7.78 g (56.3 mmol) of potassium carbonate, and 145 ml of dry dimethylformamide was added 2.592 g (13.15 mmol) of bromoacetaldehyde diethylacetal. The reaction mixture was stirred under nitrogen at 125° C. for 7.5 hr. The mixture was poured into water and extracted with ether, washed with water, dried (MgSO₄), and evaporated. The residue was chromatographed through a silica gel column using petroleum ether - ethyl acetate (21:79 v/v) to separate the diastereomers. Multiple elutions yielded 455 mg of the equatorial-methyl isomer and 1.532 g of the axial-methyl isomer of formula S above. An additional 289 mg remained as a mixture of diastereomers. Two-dimensional n.m.r. confirmed the axial and equatorial assignments.

Example 7

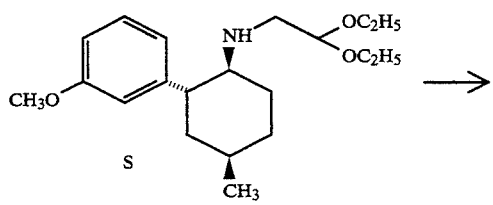

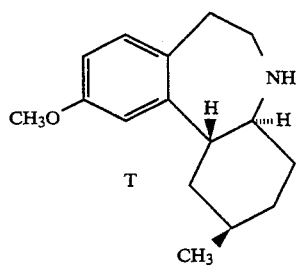

To a solution of 1.020 g (3.04 mmol) of the compound of formula S in 42 ml of trifluoroacetic acid at 0° C. was added 1.0 ml of conc. sulfuric acid dropwise. After stirring at 0° C. for 1 hr., the mixture was poured into 600 ml of cold saturated sodium bicarbonate. Sufficient solid sodium bicarbonate was added to neutralize the mixture. The mixture was extracted with methylene chloride, dried (MgSO4), and evaporated. The residue was taken up in 56 ml of absolute ethanol containing 200 mg (3.18 mmol) of sodium cyanoborohyddde and 0.2 ml of glacial acetic acid. After stirring overnight at room temperature the reaction mixture was acidified to pH 2 with 1M HCl and stirred for 30 minutes. The mixture was adjusted to pH 8-9 with 25% NaOH and the ethanol was evaporated. Water was added and the mixture was extracted with methylene chloride, dried (MgSO4), and concentrated to yield a yellow solid. The solid was taken up in 4 ml of 5% methanol in methylene chloride and passed through a plug of silica gel to remove polar contaminants. Total yield was 189 mg (24%) of an oil of formula T above. The n.m.r. spectrum confirmed the structure of formula T.

Example 8

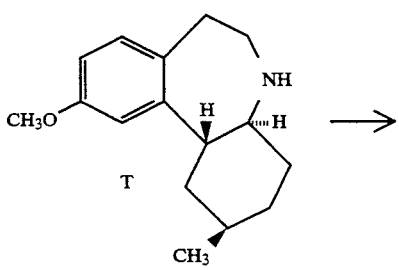

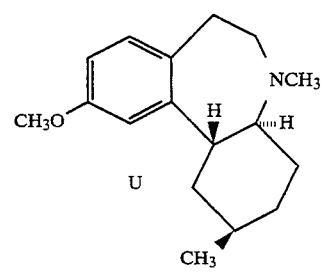

To a solution of 276 mg (1.12 mmol) of the compound of formula T in 5.5 ml of dry dimethylformamide at 0° was added 0.110 ml of 90% formic acid followed by 0.10 ml of 37.9% formaldehyde. After heating at 80° C. for 2 hr. the reaction mixture was cooled and poured into water. The solution was made basic with 20% sodium hydroxide, extracted with ether, washed with water, dried (MgSO4), and evaporated to give an oil. Chromatography on a silica gel column using methylene chloride - methanol (80:20 v/v) yielded 157 mg (54%) of an oil of formula U. The n.m.r. spectrum confirmed the structure of formula U.

Example 9

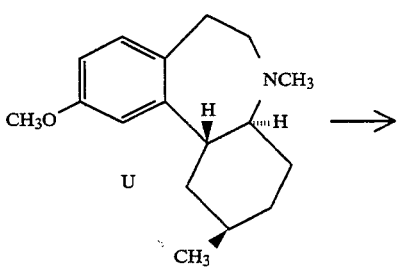

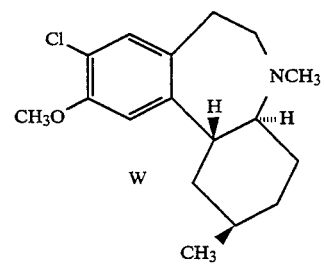

To a solution of 157 mg (0.605 mmol) of the compound of formula U in 10 ml of methylene chloride at −10° C. and under nitrogen was added a solution of methylene chloride (2.5 ml) containing 0.679 mmol (1.12 equiv.) of sulfuryl chloride over 30 minutes. After stirring overnight at room temperature, a TLC of the reaction mixture showed some starting material remaining. An additional 0.4 mmol of sulfuryl chloride was added at −10° C. and the mixture was stirred for 1.5 hr. at room temperature. The reaction mixture was poured into saturated sodium bicarbonate and extracted with methylene chloride, dried (MgSO4), and concentrated. The residue was chromatographed on silica gel using methylene chloride - methanol (90:10 v/v) to give 82 mg (46%) of a tan solid of formula W. The n.m.r. spectrum confirmed the structure of formula W.

Example 10

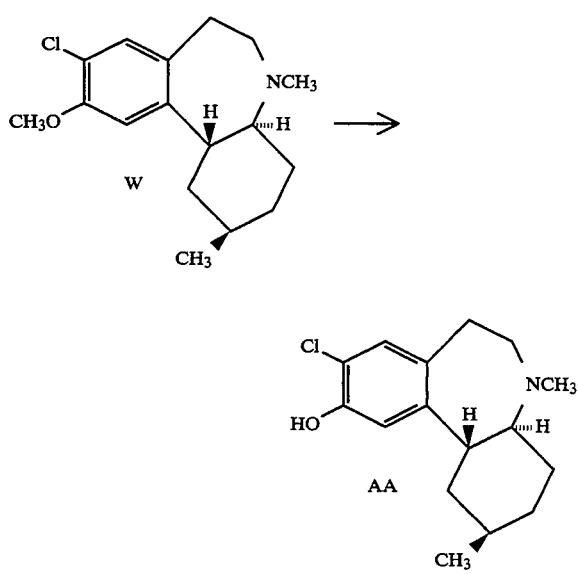

To a mixture of 60% sodium hydride (22 mg; 0.54 mmol) in 1 ml of dimethylformamide at 0° C. was added 0.040 ml (0.54 mmol) of ethanethiol dropwise via syringe. The mixture was stirred at 0° C. for 10 min. and at room temperature for 30 minutes. A solution of dimethylformamide (1 ml) containing 80 mg (0.27 mmol) of the compound of formula W was added via syringe and the mixture was heated to 95° C. for 4.5 hr. The mixture was poured into water, adjusted to pH 7-8 (NH$_4$Cl), extracted with three portions of methylene chloride, dried (MgSO$_4$), and evaporated. Preparative TLC of the residue on silica gel using methylene chloride - methanol (90:10 v/v) yielded 25 mg (33%) of the compound of formula AA. The structure was confirmed by n.m.r. and mass spec.

Preparative Example 11

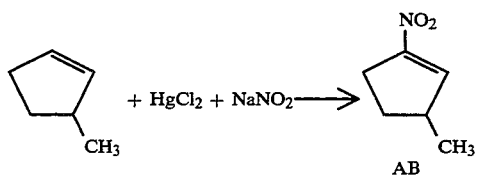

3- Methylcyclopentene (100 g), HgCl$_2$ (330 g), NaNO$_2$ (145 g) and water (2.5 l) were combined in a flask, and stirred at room temperature for 24 hrs. At the end of this time, the solids which had formed were filtered, suspended in methylene chloride, and treated with 310 ml of 2.5 N NaOH. The resulting emulsion was poured through Celite, and the organic phase of the filtrate separated, dried over Na$_2$SO$_4$, and solvent removed to give an oily solid. The product was distilled from this material at 60°-650° at 2mm Hg to give a yellow liquid product of formula AB (45 g).

Preparative Example 12

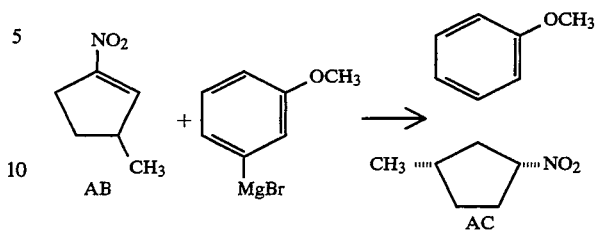

A solution of 3-bromoanisole (1.0 g) in 5 ml of dry tetrahydrofuran (THF) was added dropwise to a mixture of magnesium turnings (130 mg) in dry THF (3 ml). The reaction was allowed to proceed until the magnesium had been consumed. The resulting mixture was then cooled to $-10°$ C. and a solution of the product of formula AB of Preparative Example 11 (567 mg) in 5 ml of THF added dropwise. The mixture was then warmed to room temperature and stirred for 1 hr. The mixture was then cooled in ice and quenched with a mixture of 1:2 acetic acid: 0.1N HCl. After stirring at room temperature for 1 hr. the THF was removed under vacuum, the resulting product diluted with 25 ml of water, and the mixture extracted with ether. The extracts were separated, dried, and solvent removed to give a dark oil which was purified by flash chromatography on a 50 mm×7" column of flash grade silica gel, eluting with 9:1:0.05 hexane-ethyl acetate-triethylamine to give 150 mg of a pale yellow oil which was shown to be the product of formula AC by NMR.

Preparative Example 13

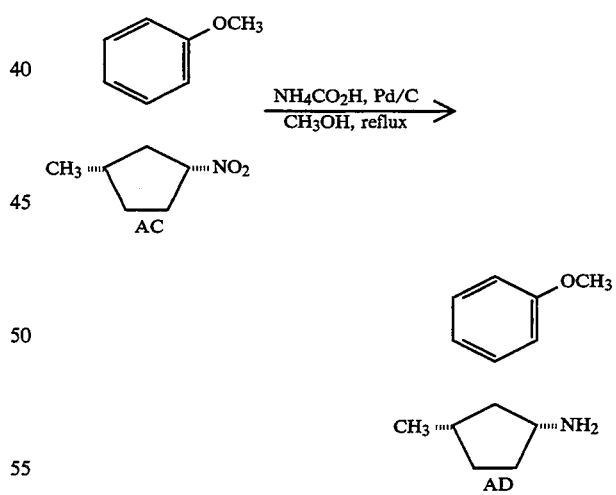

The product of formula AC of Preparative Example 12 (100 mg), ammonium formate (109 mg), methanol (5 ml), and 10% Pd/C (10 mg) were combined and stirred for 16 hrs at room temperature, and 8 . hrs at reflux. Catalyst was filtered off, and the methanolic filtrate evaporated. The oily product was dissolved in methylene chloride, washed with saturated NaHCO$_3$ solution, dried, and evapoprated to give an oil (70 mg). which was purified by chromatography on a 10 mm×6" column of flash silica gel eluting with 9:1 CH$_2$Cl$_2$—MeOH to provide the compound of formula AD.

Example 11

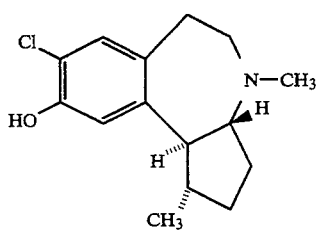

The above compound was made from the compound of formula AD of Preparative Example 13 by using essentially the same procedures as described in Preparative Example 10 and in Examples 7, 8, 9 and 10 above.

Preparative Example 14

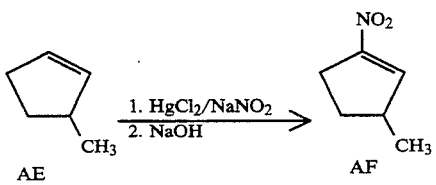

In a solution containing 130.5 g (1.89 mol) of sodium nitrite and water (2.2 L) was dissolved 297 g (1.09 mol) of mercuric chloride. To the resulting pale yellow solution was added 90 g (1.09 mol) of 3-methyl cyclopentene, and vigorous stirring at room temperature was maintained for 20 hours until precipitation of the adduct was complete. The intermediate organomercurial was separated by filtration and air dried to afford 276 g of an off-white solid.

The solid was added to methylene chloride (1 L) and 310 mL of 2-5N aqueous NaOH was added. The resulting dark emulsion was stirred for 1 hr. and the product was separated by filtration with the aid of celite. The two phases were separated and the organic phase was washed with water, dried (Na2SO4), and evaporated to give an orange oily solid. The alkene was distilled at 2 mm Hg and 60°-65° C. to give 42 g of yellow liquid. The n.m.r. spectrum indicated a mixture of regioisomers in favor of the desired isomer of formula AF above. The difficult to separate mixture was carded to the next step of Preparative Example 15 without separation.

Preparative Example 15

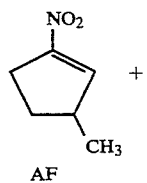

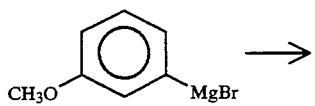

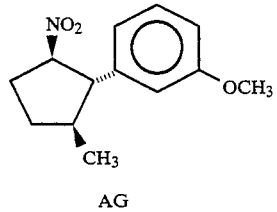

A solution of 3-bromoanisole (57-2 g, 0.31 mol) in 250 mL of THF was added dropwise to a mixture containing magnesium turnings (7-48 g, 0.31 mol) in 170 mL of THF. The mixture was allowed to stir at room temperature until the magnesium was consumed (~2 hr.). The mixture was then cooled to −10° C. and a solution containing mixture of the compound of formula AF (34.0 g, 0.27 mol) and 250 mL of THF was added dropwise. The mixture was allowed to gradually warm to room temperature and maintained at that temperature for 1 hr. The reaction was quenched by pouring the mixture into 800 mL of ice cold mixture of 1:2 acetic acid: 0.1N HCl. THF was removed under reduced pressure, 200 mL of water was added, and the resulting mixture was neutralized with saturated NaHCO3 and extracted with ether. After drying over MgSO4, the ether was evaporated to a dark brown oil. The crude product mixture was chromatographed on Waters Prep 500 eluting with 95:5 hexane:ethyl acetate to afford 10.15 g of product as yellow oil. The carbon and proton n.m.r. spectra confirmed the structure of formula AG above.

Preparative Example 16

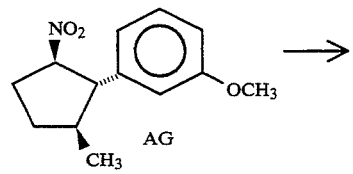

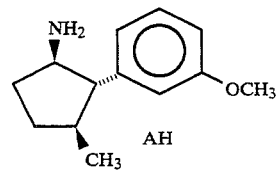

A solution containing 10.1 g (42.9 mmol) of the compound of formula AG above, 10.72 g of ammonium formate, 1.0 g of 10% palladium on carbon, and 500 ml of absolute ethanol was stirred at 70° for 12 hr. The catalyst was filtered off (celite) and the ethanol was evaporated. To the residue was added water and the mixture was neutralized with saturated NaHCO3. The mixture was extracted with methylene chloride, dried (MgSO4), and concentrated to give 9.1 g of pale yellow oil. The n.m.r. spectrum confirmed the structure of the compound of formula AH above.

Preparative Example 17

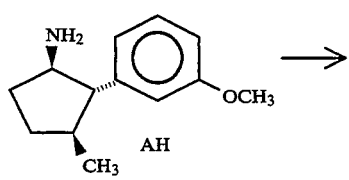

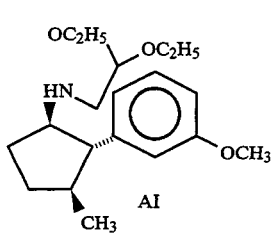

To a mixture of 9.0 g (43.9 mmol) of the compound of formula AH above, 31.0 g (219 mmol) of potassium carbonate, and 140 mL of dry dimethylformamide was added 8.8 g (44.6 mmol) of bromoacetaldehyde diethylacetal. The resulting mixture was stirred under nitrogen at 125° C. for 8 hr. The mixture was cooled to room temperature and poured into water (500 mL). Extracted with ether, washed combined organic phases with water and dried (MgSO4). Evaporation of solvent yielded 13.85 g of product as yellow oil and was used directly for Preparative Example 18 below without further purification. The n.m.r. spectrum confirmed the structure of the compound of formula Al above.

Preparative Example 18

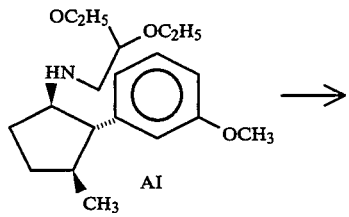

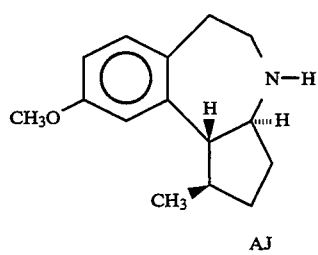

To a solution of 13.8 g (40.5 mmol) of the compound of formula Al above in methylene chloride (1.5 l) was added 162 mL of methanesulfonic acid dropwise. The resulting mixture was stirred at room temperature under nitrogen for 17 hr. The mixture was carefully poured into saturated NaH CO3 mixture and extracted with methylene chloride. After drying over MgSO4, the solvent was evaporated to give 12.1 g of crude enamine.

The product was taken up in ethanol (1.1 L) containing 3.64 g (57.9 mmol) of sodium cyanoborohydride and 3.2 ml of glacial acetic acid. After stirring for 12 hr. at room temperature the mixture was neutralized with 10% NaHCO3. The ethanol was removed under reduced pressure and the aqueous residue was extracted with methylene chloride. Dried over MgSO4 and evaporated to afford 12.05 g of product of formula AJ above as semi-solid foam which was used as is in the procedure of Preparative Example 19 below.

Preparative Example 19

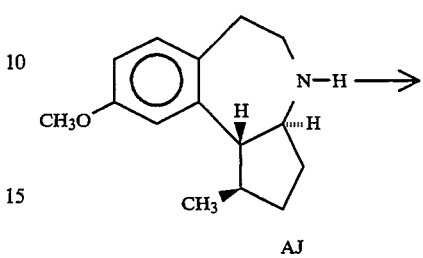

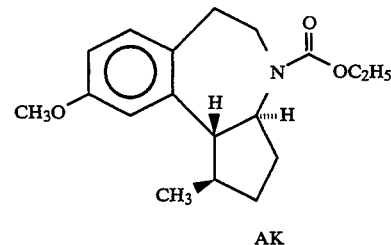

To a mixture containing 12.0 g (51.9 mmol) of the compound of formula AJ above, acetonitrile (450 mL) and 6.2 g of sodium bicarbonate cooled in an ice bath was added 5.6 g (52.0 mmol) of ethyl chloroformate dropwise. The reaction mixture was allowed to warm gradually to room temperature overnight. Quenched with water, removed acetonitrile at reduced pressure and the residual aqueous phase was extracted with ethyl acetate (3×250 mL). The combined organic phases were washed with water, brine (200 ml each) and dried over MgSO4. Evaporated solvent to give 12.2 g of brown oil. Chromatography on a silica gel column eluting with ethyl acetate:hexanes (80:20) yielded 3.7 g of an oil. The n.m.r. spectrum confirmed the structure of the compound of formula AK above.

Preparative Example 20

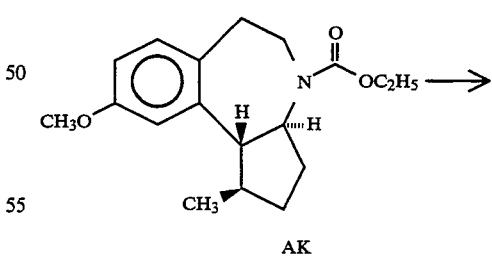

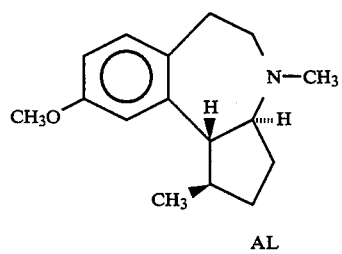

To a solution containing 3.7 g (12.2 mmol) of the compound of formula AK above and THF (100 mL) was added 600 mg (15.8 mmol) of lithium aluminum hydride portion wise. The resulting mixture was heated at reflux for 8 hr. After cooling to room temperature the reaction mixture was quenched by sequential addition of 1.3 mL of water, 1.3 mL of 15% NaOH, followed by 5.3 mL of water. The resulting mixture was stirred for 1 hr. and filtered through a pad of celite. Washed the precipitate with THF several times and the filtrate was evaporated. Chromatography on silica gel column eluting with CH$_2$Cl$_2$: MeOH:NH$_4$OH (80:3:1) afforded 565 mg of product as yellow oil. The n.m.r. spectrum confirmed the structure of the compound of formula AL above.

Preparative Example 21

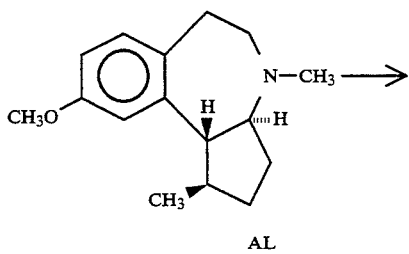

AL

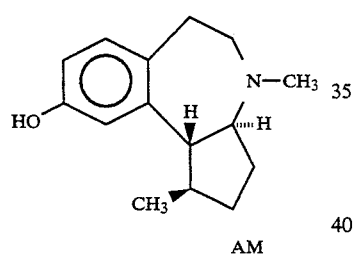

AM

A solution containing 550 mg (2.2 mmol) of the compound of formula AL above, 3 mL of glacial acetic acid and 10 mL of 48% hydrobromic acid was heated at 120° C. for 6 hr. After cooling to room temperature the mixture was poured into water (100 mL). Neutralized with saturated NaHCO$_3$ and extracted with methylene chloride (3×75 mL). Dried over MgSO$_4$ and evaporated to give 500 mg of pure product. The n.m.r. spectrum confirmed the structure of the compound of formula AM above.

Preparative Example 22

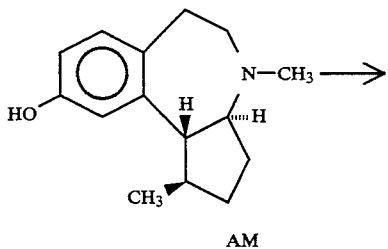

AM

-continued

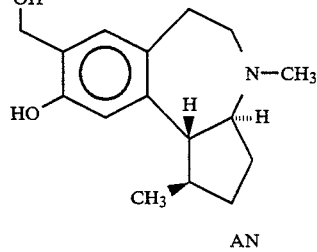

AN

A homogenous mixture containing 540 mg (2.3 mmol) of the compound of formula AM above, 12.5 mL of 37% aqueous formaldehyde, 11.5 mL of 4% aqueous KOH and 35 mL of dimethoxyethane was heated at 80° for 3 hr. under blanket of nitrogen. The mixture was then allowed to cool to room temperature and brought to pH 8 with 10% HCl. The volatile solvents were removed under reduced pressure and the aqueous residue was extracted with chloroform. The combined organic phases were dried over Na$_2$SO$_4$ and concentrated to afford 510 mg of product as yellow oil. The n.m.r. spectrum confirmed the structure of the compound of formula AN above.

Preparative Example 23

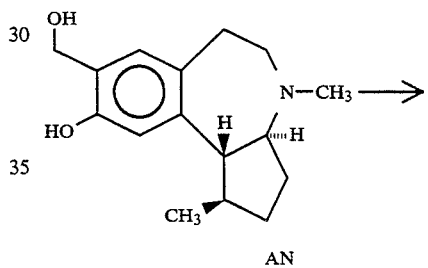

AN

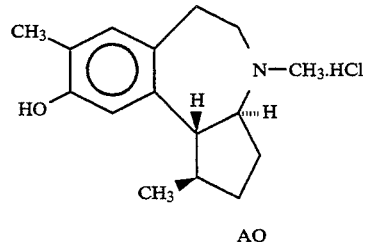

AO

A mixture containing 510 mg (1.9 mmol) of the compound of formula AN above, 132 mg of p-toluene sulfonic acid, 250 mg of 20% palladium on carbon, and 35 mL of glacial acetic acid was placed in a Parr shaker apparatus under 60 psi of hydrogen for 20 hr. The resulting mixture was filtered through celite to remove the catalyst and the acetic acid was evaporated. Aqueous saturated NaHCO$_3$ (30 ml) was added and the aqueous phase extracted with methylene chloride. The organic phase was dried over Na$_2$SO$_4$ and concentrated to yellow oil. Chromatography on silica gel column eluting with CH$_2$Cl$_2$: MeOH:NH$_4$OH (200:7:1) afforded 225 mg of product as yellow oil. The product was taken-up in ether and treated with ethereal HCl. Filtered and vacuum dried to afford 210 mg of the hydrochloride salt of formula AO above. m.p. 181°–187° C.

By substituting the starting material listed in column 2 of Table 2 below, the products listed in column 3 were also prepared by following basically the same procedures as described in column 1 of Table 2:

TABLE 2

| Preparative Procedures | Starting material | Product |
|---|---|---|
| Preparative Examples 5-10 and Examples 7-8 | | |
| Preparative Examples 1-4 and Examples 1-6 | | |

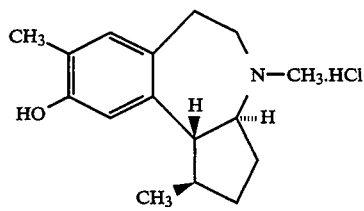

The following formulations exemplify some of the dosage forms of the compositions of this invention. In each, the term "active compound" refers to of the formula:

However, this compound may be replaced by equally effective amounts of other compounds of the invention as described above.

EXAMPLE A

| | Tablets | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weigh on a suitable tablet machine.

EXAMPLE B

| | | Capsules | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the structural formula

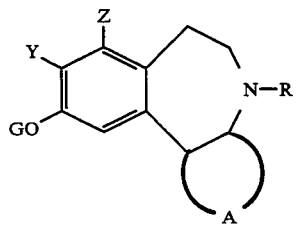

or a pharmaceutically acceptable salt thereof, wherein R represents H, alkyl, allyl or

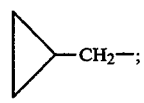

A represents —$_n$—;

n represents 3 or 4;

R¹ and R² may be the same or different and each independently represents H, OH, alkyl, alkoxy, phenyl or substituted phenyl, with the proviso that R¹ and R² on the same carbon atom are not both OH, or R¹ and R² on the same carbon atom together represent=O;

G represents H, R³(CO)— or ArNHCO—;

R³ represents H, alkyl, alkoxy, phenyl or substituted phenyl;

Ar represents phenyl or substituted phenyl; and

Y and Z may be the same or different and each is independently selected from H, halo, alkyl, alkoxy or haloalkyl.

2. A compound according to claim 1, wherein ring A represents

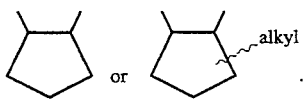

3. A compound according to claim 1, wherein ring A represents

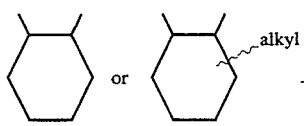

4. A compound according to claim 1 wherein R is methyl.

5. A compound according to claim 1 wherein Z is H or chloro.

6. A compound according to claim 1 wherein Y is chloro or methyl.

7. A compound according to claim 1 wherein G represents H or ArNHCO—.

8. A compound according to claim 1 having the structural formula

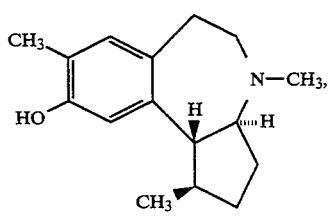

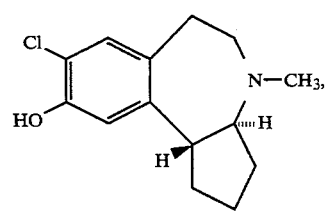

-continued

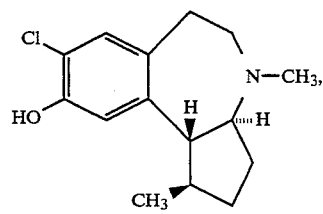

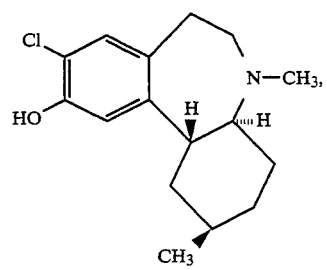

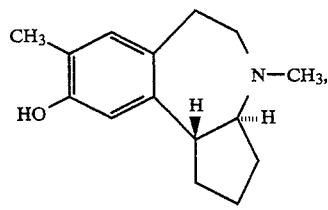

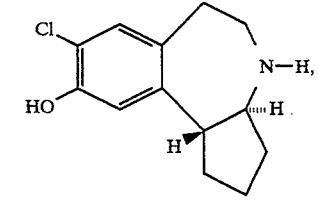

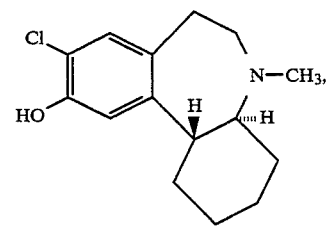

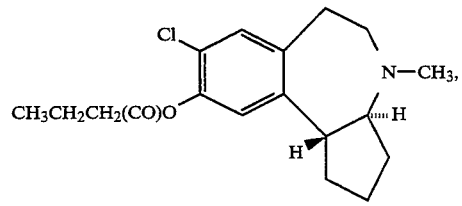

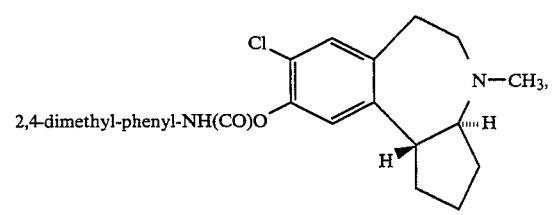

-continued

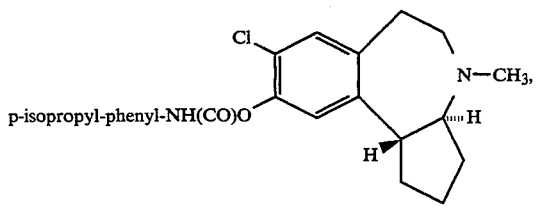

or a pharmaceutically acceptable salt of such a compound.

9. A pharmaceutical composition for treating psychoses, drug dependence, D1 dependent neurological disorder or pain in mammals comprising administering to a mammal in need of such treatment an effective amount of a compound of claim 1 in a pharmaceutically acceptable carrier.

10. A pharmaceutical composition as claimed in claim 9, said composition being in dosage form.

11. A method for treating psychoses, drug dependence, D 1 dependent neurological disorder or pain comprising administering to a mammal in need of such treatment an effective amount of a compound of claim 1.

* * * * *